US012722011B2

(12) United States Patent
Weerakoon et al.

(10) Patent No.: US 12,722,011 B2
(45) Date of Patent: Sep. 1, 2026

(54) ALGORITHM FOR ADJUSTING A COMPLIANCE VOLTAGE IN A STIMULATOR DEVICE HAVING NEURAL SENSING CAPABILITY

(71) Applicant: Boston Scientific Neuromodulation Corporation, Valencia, CA (US)

(72) Inventors: Pujitha Weerakoon, Valencia, CA (US); Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 641 days.

(21) Appl. No.: 18/152,636

(22) Filed: Jan. 10, 2023

(65) Prior Publication Data

US 2023/0248978 A1 Aug. 10, 2023

Related U.S. Application Data

(60) Provisional application No. 63/266,806, filed on Jan. 14, 2022.

(51) Int. Cl.
*A61N 1/36* (2006.01)

(52) U.S. Cl.
CPC ..... *A61N 1/36139* (2013.01); *A61N 1/36153* (2013.01); *A61N 1/36157* (2013.01)

(58) Field of Classification Search
CPC ............ A61N 1/36139; A61N 1/36153; A61N 1/36157; A61N 1/36125; A61N 1/36135
See application file for complete search history.

(56) References Cited

U.S. PATENT DOCUMENTS 4,811,738 A 3/1989 Economides et al.
5,697,958 A 12/1997 Paul et al.
(Continued)

FOREIGN PATENT DOCUMENTS

WO 95/07114 3/1995
WO 2013/109603 7/2013
(Continued)

OTHER PUBLICATIONS

U.S. Appl. No. 63/264,281, filed Dec. 2, 2021.
(Continued)

*Primary Examiner* — John R Downey
*Assistant Examiner* — Karmel J Webster
(74) *Attorney, Agent, or Firm* — Lewis & Reese, PLLC

(57) ABSTRACT

An optimization algorithm is disclosed for optimizing an implantable pulse generator. The algorithm is particularly useful when one or more of the electrodes (e.g., the case electrode) is used to provide a common mode voltage (Vcm) to the tissue, which assists in sensing neural responses to the stimulation. The algorithm preferably optimizes both the compliance voltage VH used to power the simulation circuitry, and the strength of tissue driver circuitry used to provide Vcm to the tissue. The algorithm preferably considers information determined by VH measurement circuitry (which informs as to the ability to form prescribed stimulation pulses without loading), sensing monitoring circuitry (which informs as to the magnitude of the inputs of the sensing circuitry), and/or tissue monitoring circuitry (which informs as to adequacy of the strength of the tissue driver circuitry).

17 Claims, 14 Drawing Sheets

(56) References Cited

U.S. PATENT DOCUMENTS 5,702,429 A 12/1997 King
5,902,236 A 5/1999 Iversen
5,902,249 A 5/1999 Lyster
5,913,882 A 6/1999 King
6,181,969 B1 1/2001 Gord
6,516,227 B1 2/2003 Meadows et al.
6,560,490 B2 5/2003 Grill et al.
7,024,247 B2 4/2006 Gliner et al.
7,424,322 B2 9/2008 Lombardi et al.
7,444,181 B2 10/2008 Shi et al.
7,450,992 B1 11/2008 Cameron
8,255,057 B2 8/2012 Fang et al.
8,335,664 B2 12/2012 Eberle
8,352,030 B2 1/2013 Denison
8,606,362 B2 12/2013 He et al.
8,620,436 B2 12/2013 Parramon et al.
9,044,155 B2 6/2015 Strahl
9,061,140 B2 6/2015 Shi et al.
9,155,891 B2 10/2015 Archer
9,155,892 B2 10/2015 Parker et al.
9,174,051 B2 11/2015 Marnfeldt et al.
9,248,274 B2 2/2016 Troosters et al.
9,248,279 B2 * 2/2016 Chen .................. A61N 1/36146
9,259,574 B2 2/2016 Aghassian et al.
9,265,431 B2 2/2016 Hincapie Ordonez et al.
9,302,112 B2 4/2016 Bornzin et al.
9,314,632 B2 4/2016 Marnfeldt et al.
9,381,356 B2 7/2016 Parker et al.
9,386,934 B2 7/2016 Parker et al.
9,403,013 B2 8/2016 Walker et al.
9,409,020 B2 8/2016 Parker
9,468,765 B2 10/2016 Archer
9,526,897 B2 12/2016 Chen et al.
9,533,148 B2 1/2017 Carcieri et al.
9,604,061 B2 3/2017 Archer
9,724,508 B2 8/2017 Lamont et al.
9,731,116 B2 8/2017 Chen
9,872,990 B2 1/2018 Parker et al.
9,974,455 B2 5/2018 Parker et al.
10,076,667 B2 9/2018 Kaula et al.
10,525,252 B2 * 1/2020 Feldman ................ A61N 1/025
10,632,300 B2 4/2020 Wagenbach et al.
10,716,937 B2 7/2020 Feldman et al.
10,792,491 B2 10/2020 Feldman et al.
10,912,942 B2 2/2021 Weerkoon et al.
11,040,192 B2 6/2021 Weerakoon et al.
11,040,202 B2 6/2021 Marnfeldt
2002/0156513 A1 10/2002 Borkan
2005/0090756 A1 4/2005 Wolf et al.
2005/0246004 A1 11/2005 Cameron et al.
2006/0271118 A1 11/2006 Libbus et al.
2008/0146894 A1 6/2008 Bulkes et al.
2012/0092031 A1 4/2012 Shi et al.
2012/0095519 A1 4/2012 Parramon et al.
2012/0095529 A1 4/2012 Parramon et al.
2013/0289665 A1 * 10/2013 Marnfeldt ............ A61N 1/3782
607/62
2014/0194772 A1 7/2014 Single et al.
2014/0236042 A1 8/2014 Parker et al.
2014/0296737 A1 10/2014 Parker et al.
2015/0080982 A1 3/2015 Funderburk
2015/0157861 A1 6/2015 Aghassian
2015/0231402 A1 8/2015 Aghassian
2015/0282725 A1 10/2015 Single et al.
2015/0313487 A1 11/2015 Single et al.
2015/0360038 A1 12/2015 Zottola et al.
2016/0166164 A1 6/2016 Obradovic et al.
2016/0287126 A1 10/2016 Parker et al.
2016/0287182 A1 10/2016 Single et al.
2017/0001003 A1 * 1/2017 Pivonka ............. A61N 1/36067
2017/0049345 A1 2/2017 Single et al.
2017/0071490 A1 3/2017 Parker et al.
2017/0135624 A1 5/2017 Parker et al.
2017/0216587 A1 8/2017 Parker et al.
2017/0216600 A1 8/2017 Feldman et al.
2017/0296823 A1 10/2017 Hershey et al.
2017/0361101 A1 12/2017 Single et al.
2018/0071520 A1 3/2018 Weerakoon et al.
2018/0071527 A1 3/2018 Feldman et al.
2018/0110987 A1 4/2018 Parker et al.
2018/0117335 A1 5/2018 Parker et al.
2018/0132747 A1 5/2018 Parker et al.
2018/0132760 A1 5/2018 Parker et al.
2018/0133459 A1 5/2018 Parker et al.
2018/0140831 A1 5/2018 Feldman et al.
2018/0228391 A1 8/2018 Parker et al.
2018/0228547 A1 8/2018 Parker et al.
2018/0256052 A1 9/2018 Parker et al.
2019/0083796 A1 * 3/2019 Weerakoon ............ A61N 1/025
2019/0099602 A1 * 4/2019 Esteller .............. A61N 1/37241
2019/0175915 A1 6/2019 Brill et al.
2019/0209844 A1 7/2019 Esteller et al.
2019/0275331 A1 9/2019 Zhu et al.
2019/0290900 A1 9/2019 Esteller et al.
2019/0299006 A1 * 10/2019 Marnfeldt .......... A61N 1/36125
2019/0366094 A1 12/2019 Esteller et al.
2020/0009394 A1 * 1/2020 Huertas Fernandez ......................
A61N 1/025
2020/0155019 A1 5/2020 Esteller et al.
2020/0251899 A1 8/2020 Parks et al.
2020/0305744 A1 * 10/2020 Weerakoon .......... A61B 5/4848
2020/0305745 A1 * 10/2020 Wagenbach ....... A61N 1/36062
2021/0008373 A1 * 1/2021 Single .................. A61N 1/0551
2021/0023374 A1 * 1/2021 Block ................ A61N 1/36139
2021/0236829 A1 8/2021 Zhang et al.
2022/0040486 A1 2/2022 Moffitt

FOREIGN PATENT DOCUMENTS

WO 2015/077362 5/2015
WO 2017/100866 6/2017
WO 2017/173493 10/2017
WO 2017/210352 12/2017
WO 2017/219096 12/2017
WO 2021/046120 3/2021

OTHER PUBLICATIONS

U.S. Appl. No. 18/049,525, filed Oct. 25, 2022, Marnfeldt.

H. Mino & J. Rubenstein, "Effects of Neural Refractoriness on Spatio-Temporal Variability in Spike Initiations with Electrical Stimulation," IEEE Trans. On Neural Sys. & Rehabilitation Eng., vol. 14, No. 3, pp. 273-280 (2006).

M. Moffit et al., A Novel 3-Dimensional Algorithm for Model-Based Programming in Spinal Cord Stimulation (SCS): Illumina-3D™, presentation (2013).

M. Hughes, "Fundamentals of Clinical ECAP Measures in Cochlear Implants: Part 1: Use of the ECAP in Speech Processor Programming (2nd Ed.)," Audiology Online (Nov. 8, 2010) (http:// www.audiologyonline.com/ articles/ fundamentalsclinicalecapmeasuresin846).

I. Akhoun et al., "Electrically evoked compound action potential artifact rejection by independent component analysis: Technique validation," Hearing Research 302, pp. 60-73 (2013).

J. Rubinstein et al., "Pseudospontaneous activity: stochastic independence of auditory nerve fibers with electrical stimulation," Hear Res., 127(1-2), pp. 108-118 (1999) (abstract only).

J. Paz, "Physiological Midline Mapping Based on Spinal Cord Stimulation (SCS) Response Using the 32-Contact Paddle Lead," 19$^{th}$ NANS Annual Meeting (Dec. 13-15, 2015).

E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).

J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).

A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).

(56) References Cited

OTHER PUBLICATIONS

International Search Report and Written Opinion regarding corresponding PCT Application No. PCT/US2023/060412, mailed Apr. 3, 2023.

* cited by examiner

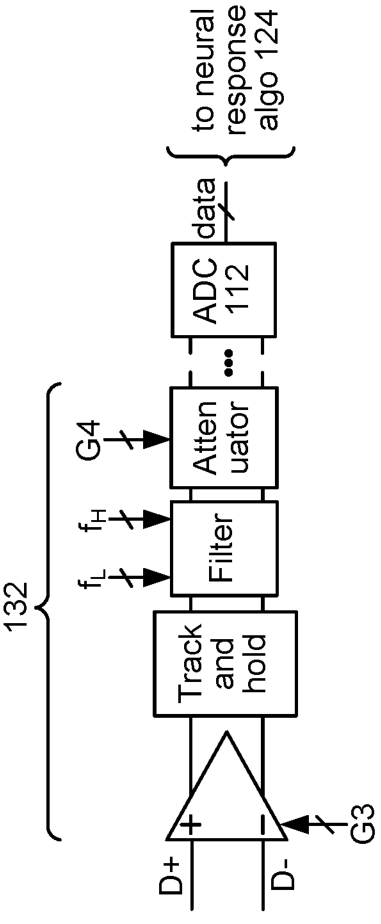
*Figure 8B*
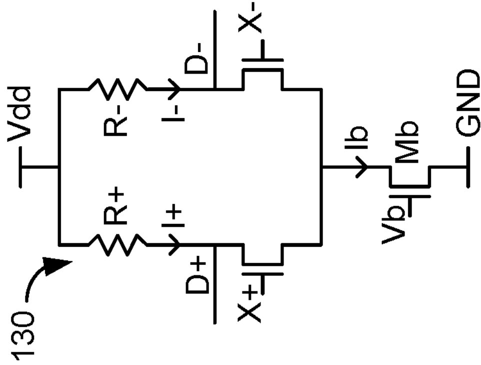

ALGORITHM FOR ADJUSTING A COMPLIANCE VOLTAGE IN A STIMULATOR DEVICE HAVING NEURAL SENSING CAPABILITY

CROSS REFERENCE TO RELATED APPLICATIONS

This is a non-provisional application of U.S. Provisional Patent Application Ser. No. 63/266,806, filed Jan. 14, 2022, which is incorporated herein by reference, and to which priority is claimed.

FIELD OF THE INVENTION

This application relates to Implantable Medical Devices (IMDs), and more specifically to circuitry to assist with sensing neural responses to stimulation in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) or Deep Brain Stimulation (DBS) system. However, the present invention may find applicability with any stimulator device system.

A stimulator system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12, or some conductive portion of the case, can also comprise an electrode (Ec). In an SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In a DBS application, the electrode leads are implanted in the brain through holes in the skull, and lead extension are used to connect the leads to the IPG which is typically implanted under the clavicle (collarbone). In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. SCS therapy can relieve symptoms such as chronic back pain, while DBS therapy can alleviate Parkinsonian symptoms such as tremor and rigidity. IPG 10 as described should be understood as including External Trial Stimulators (ETSs), which mimic operation of the IPG 10 during trials periods when leads have been implanted in the patient but the IPG 10 has not. See, e.g., U.S. Pat. No. 9,259,574 (disclosing an ETS).

IPG 10 can include an antenna 27*a* allowing it to communicate bi-directionally with a number of external devices discussed subsequently. Antenna 27*a* as shown comprises a conductive coil within the case 12, although the coil antenna 27*a* can also appear in the header 23. When antenna 27*a* is configured as a coil, communication with external devices preferably occurs using near-field magnetic induction. IPG 10 may also include a Radio-Frequency (RF) antenna 27*b*. In FIG. 1, RF antenna 27*b* is shown within the header 23, but it may also be within the case 12. RF antenna 27*b* may comprise a patch, slot, or wire, and may operate as a monopole or dipole. RF antenna 27*b* preferably communicates using far-field electromagnetic waves, and may operate in accordance with any number of known RF communication standards, such as Bluetooth, Zigbee, WiFi, MICS, and the like.

Stimulation in IPG 10 is typically provided by pulses each of which may include a number of phases (30*i*), as shown in the example of FIG. 2A. Stimulation parameters typically include amplitude (current I, although a voltage amplitude V can also be used); frequency (F); pulse width (PW); the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as an anode (during its first phase 30*a*), and thus provides pulses which source a positive current of amplitude +I to the tissue. Electrode E2 has been selected as a cathode (again during first phase 30*a*), and thus provides pulses which sink a corresponding negative current of amplitude −I from the tissue. This is an example of bipolar stimulation, in which the lead includes one anode pole and one cathode pole. Note that more than one electrode on the lead may be selected to act as an anode electrode to form an anode pole at a given time, and more than one electrode may be selected to act as a cathode to form a cathode pole at a given time, as explained further in U.S. Pat. No. 10,881,859. Stimulation provided by the IPG 10 can also be monopolar. In monopolar stimulation, the lead is programmed with a single pole of a given polarity (e.g., a cathode pole), with the conductive case electrode Ec acting as a return (e.g., an anode pole). Again, more than one electrode on the lead may be active to form the pole during monopolar stimulation.

IPG 10 as mentioned includes stimulation circuitry 28 to form prescribed stimulation at a patient's tissue. FIG. 3 shows an example of stimulation circuitry 28, which includes one or more current source circuits and one or more current sink circuits. The sources and sinks can comprise Digital-to-Analog converters (DACs), and may be referred to as PDACs and NDACs in accordance with the Positive (sourced, anodic) and Negative (sunk, cathodic) currents they respectively issue. In the example shown, a NDACi/PDACi pair is dedicated (hardwired) to a particular electrode node ei 39. Each electrode node ei 39 is associated with an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation as explained above. PDACs and NDACs can also comprise voltage sources.

Proper control of the PDACs and NDACs allows any of the electrodes 16 to act as anodes or cathodes to create a current through a patient's tissue, R, hopefully with good therapeutic effect. Consistent with the example provided in FIG. 2A, FIG. 3 shows operation during the first phase 30*a* in which electrode E1 has been selected as an anode electrode to source current I to the tissue R and E2 has been selected as a cathode electrode to sink current from the tissue. Thus PDAC1 and NDAC2 are digitally programmed to produce the desired current, I, with the correct timing (e.g., in accordance with the prescribed frequency and pulse widths). As mentioned above, more than one anode electrode and more than one cathode electrode may be selected at one time, and thus current can flow through the tissue R between two or more of the electrodes 16. Other stimulation circuitries 28 can also be used in the IPG 10, including ones that includes switching matrices between the electrode nodes ei 39 and the N/PDACs. See, e.g., U.S. Pat. Nos. 6,181,969, 8,606,362, 8,620,436, 11,040,192, and 10,912,942. Much of the stimulation circuitry 28 of FIG. 3, including the PDACs and NDACs, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as IPG master control circuitry 102 (see FIG. 5), telemetry circuitry (for interfacing off chip with telemetry antennas 27*a* and/or 27*b*), circuitry for generating the compliance voltage VH (as explained next), various measurement circuits, etc.

Power for the stimulation circuitry 28 is provided by a compliance voltage VH, as described in further detail in U.S. Patent Application Publications 2013/0289665 and 2018/0071520, and PCT (Int'l) Patent Application Publication WO 2021/046120. The compliance voltage VH may be coupled to the source circuitry (e.g., the PDAC(s)), while ground may be coupled to the sink circuitry (e.g., the NDAC(s)), such that the stimulation circuitry 28 is powered by VH and ground. Other power supply voltages may be used with the PDACs and NDACs, and explained in U.S. Patent Application Publication 2018/0071520, but these aren't shown in FIG. 3 for simplicity.

Preferably, and as described in U.S. Pat. No. 11,040,202, the compliance voltage VH can be produced by a VH regulator 49. VH regulator 49 receives the voltage of the battery 14 (Vbat) and boost this voltage to a higher value required for the compliance voltage VH. VH regulator 49 can comprise an inductor-based boost converter or a capacitor-based charge pump for example.

The VH regulator 49 can vary the value of VH based on measurements taken from the stimulation circuitry 28. As explained in detail in the '202 patent, VH measurement circuitry 51 can be used to measure the voltage drops across the active DACs (e.g., PDAC1 (Vp1) and NDAC2 (Vn2) in the example shown in FIG. 3) in the stimulation circuitry 28. These measured values can be compared in the VH measurement circuitry 51 to minimum values. For example, all measured voltage drops Vpi can be compared to Vp(min), and all measured voltage drops Vni can be compared to Vn(min). The values for Vp(min) and Vn(min) may be programmable or adjustable.

If one or more measured values are found to be below its associated minimum (e.g., Vp1<Vp(min)), there is a risk that the corresponding DAC (e.g., PDAC1) is not receiving enough power, and hence will not be able to provide the programmed current. In short, the DAC is said to be loaded, and will produce less than the programmed current. This suggests that VH should be raised to a higher value, and thus the measurement circuitry can inform the VH regulator 49 to increase VH via one or more control signals M. By contrast, if all measured values are found to be higher than their associated minimum, then VH is sufficient to provide the programmed current, but also may higher than necessary. In this circumstance, it may be reasonable to lower the value for VH, which can be affect via control signal(s) M.

Such measurements thus allow VH to be adjusted in a closed loop manner that is high enough to form the programmed current without loading, yet low enough to not needlessly waste power in the stimulation circuitry 28 when forming the prescribed current. VH can therefore be variable, and typically ranges from about 5 to 15 Volts. VH measurement circuitry 51 may comprise logic circuitry and may be formed at least in part in control circuitry 102 within the IPG 10, although it may also comprise analog components such as comparators or amplifiers, as shown for example in U.S. Pat. No. 10,525,252. Measured voltage drops Vpi and Vni can also be compared to maximum values Vp(max) and Vn(max) as described in the '202 patent, although this detail isn't shown.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861. While useful, DC-blocking capacitors 38 are not strictly required in all IPG designs and applications.

Referring again to FIG. 2A, the stimulation pulses as shown are biphasic, with each pulse comprising a first phase 30*a* followed thereafter by a second phase 30*b* of opposite polarity. Biphasic pulses are useful to actively recover any charge that might be stored on capacitive elements in the electrode current paths, such as on the DC-blocking capacitors 38. Active charge recovery is shown with reference to both FIGS. 2A and 2B. During the first pulse phase 30*a*, charge will (primarily) build up across the DC-blockings capacitors C1 and C2 associated with the electrodes E1 and E2 used to produce the current, giving rise to voltages Vc1 and Vc2 ($I=C*dV/dt$). During the second pulse phase 30*b*, when the polarity of the current I is reversed at the selected electrodes E1 and E2, the stored charge on capacitors C1 and C2 is recovered, and thus voltages Vc1 and Vc2 will ideally return to 0V at the end the second pulse phase 30*b* if the pulse phases 30*a* and 30*b* are charge balanced.

Charge recovery using phases 30*a* and 30*b* is said to be "active" because the P/NDACs in stimulation circuitry 28 actively drive a current, in particular during the last phase 30*b* to recover charge stored after the first phase 30*a*. However, such active charge recovery may not be perfect, and some residual charge may be present in capacitive elements even after phase 30*b* is completed. Accordingly, the stimulation circuitry 28 can also provide for passive charge recovery. Passive charge recovery is implemented using passive charge recovery switches PRi as shown in FIG. 3, and can occur during periods 30*c* after the last active pulse phase (e.g., 30*b*). Passive charge recovery is explained further in U.S. Pat. Nos. 10,716,937 and 10,792,491, which are incorporated herein by reference. A quiet phase 30*d* during which no stimulation is applied may follow passive charge recovery (30*c*) is desired, which proceeds a next-active phase (e.g., 30*a*).

FIG. 4 shows various external systems 60, 70, and 80 that can wirelessly communicate data with the IPG 10. Such systems can be used to wirelessly transmit a stimulation program to the IPG 10—that is, to program its stimulation circuitry 28 to produce stimulation with desired amplitudes and timings as described earlier. Such systems may also be used to adjust one or more stimulation parameters of a stimulation program that the IPG 10 is currently executing, and/or to wirelessly receive information from the IPG 10, such as various status information, etc.

External controller 60 can be as described in U.S. Patent Application Publication 2015/0080982 for example, and may comprise a portable, hand-held controller dedicated to work with the IPG 10. External controller 60 may also comprise a general-purpose mobile electronics device such as a mobile phone which has been programmed with a Medical Device Application (MDA) allowing it to work as a wireless controller for the IPG 10, as described in U.S. Patent Application Publication 2015/0231402. External controller 60 includes a display 61 and a means for entering commands, such as buttons 62 or selectable graphical icons provided on the display 61. The external controller 60's user interface enables a patient to adjust stimulation parameters, although it may have limited functionality when compared to systems 70 and 80, described shortly. The external controller 60 can have one or more antennas capable of communicating with a compatible antenna in the IPG 10, such as a near-field magnetic-induction coil antenna 64*a* and/or a far-field RF antenna 64*b*.

Clinician programmer 70 is described further in U.S. Patent Application Publication 2015/0360038, and can comprise a computing device such as a desktop, laptop, or notebook computer, a tablet, a mobile smart phone, a Personal Data Assistant (PDA)-type mobile computing device, etc. In FIG. 4, the computing device is shown as a laptop computer that includes typical computer user interface means such as a display 71, buttons 72, as well as other user-interface devices such as a mouse, a keyboard, speakers, a stylus, a printer, etc., not all of which are shown for convenience. Also shown in FIG. 4 are accessory devices for the clinician programmer 70 that are usually specific to its operation as a stimulation controller. A communication "wand" 76 coupleable to suitable ports on the computing device can include an IPG-compliant antenna such as a coil antenna 74*a* or an RF antenna 74*b*. The computing device itself may also include one or more RF antenna 74*b*. The clinician programmer 70 can also communicate with other devices and networks, such as the Internet, either wirelessly or via a wired link provided at an Ethernet or network port.

External system 80 comprises another means of communicating with and controlling the IPG 10 via a network 85 which can include the Internet. The network 85 can include a server 86 programmed with communication and control functionality, and may include other communication networks or links such as WiFi, cellular or land-line phone links, etc. The network 85 ultimately connects to an intermediary device 82 having antennas suitable for communication with the IPG's antenna, such as a near-field magnetic-induction coil antenna 84*a* and/or a far-field RF antenna 84*b*. Intermediary device 82 may be located generally proximate to the IPG 10. Network 85 can be accessed by any user terminal 87, which typically comprises a computer device associated with a display 88. External system 80 allows a remote user at terminal 87 to communicate with and control the IPG 10 via the intermediary device 82.

FIG. 4 also shows circuitry 90 involved in any of external systems 60, 70, or 80. Such circuitry can include control circuitry 92, which can comprise any number of devices such as one or more microprocessors, microcomputers, FPGAs, DSPs, other digital logic structures, etc., which are capable of executing programs in a computing device. Such control circuitry 92 may contain or coupled with memory 94 which can store external system software 96 for controlling and communicating with the IPG 10, and for rendering a Graphical User Interface (GUI) 99 on a display (61, 71, 88) associated with the external system. In external system 80, the external system software 96 would likely reside in the server 86, while the control circuitry 92 could be present in either or both the server 86 or the terminal 87.

SUMMARY

A method is disclosed for operating a stimulator device having a plurality of electrodes comprising at least one sensing electrode, at least two stimulation electrodes, and at least one common mode electrode. The method may comprise: receiving signals from a patient's tissue at the at least one sensing electrode, and providing the received signal to at least one input of a sense amp circuit; providing a common mode voltage to the tissue at the at least one common mode electrode, wherein a tissue current at the common mode electrode is limited to a programmable first magnitude; executing a stimulation program to provide a stimulation current of a prescribed amplitude between the at least two stimulation electrodes and through the patient's tissue using stimulation circuitry powered by a compliance voltage; generating either or both of at least one first control signal indicating whether the tissue current has reached the first magnitude, or at least one second control signal indicating whether a second magnitude at the at least one input is appropriate for sensing the signals from the patient's tissue; generating at least one third control signal indicating whether the stimulation current is provided by the stimulation circuitry at the prescribed amplitude without loading; and executing an algorithm in the stimulator device, wherein the algorithm is configured to use the at least one third control signal and either or both of the at least one first control signal and the at least one second control signal to adjust the compliance voltage.

In one example, the algorithm is configured to adjust the compliance voltage to a lowest value at which the stimulation current is provided by the stimulation circuitry at the prescribed amplitude without loading; and either or both of the following occurs: the tissue current has not reached the first magnitude, or the second magnitude at the at least one input is appropriate for sensing the signals from the patient's tissue.

In one example, the algorithm is configured to initially to set the compliance voltage to a maximum voltage. In one example, the algorithm is configured to use the at least one third control signal and either or both of the at least one first control signal and the at least one second control signal to reduce the compliance voltage to the lowest value. In one example, the algorithm is configured to adjust the compliance voltage using the at least one third control signal and the at least one first control signal. In one example, the algorithm is configured to adjust the compliance voltage using the at least one third control signal and the at least one second control signal. In one example, the algorithm is configured to adjust the compliance voltage using the at least one third control signal, the at least one first control signal, and the at least one second control signal. In one example, the algorithm is further configured to use either or both of the at least one first control signal and the at least one second control signal to adjust the first magnitude. In one example, the algorithm is configured to adjust the first magnitude to a lowest value at which either or both of the following occurs: the tissue current has not reached the first magnitude, or the second magnitude at the at least one input is appropriate for sensing the signals from the patient's tissue. In one example, the algorithm is configured to adjust the compliance voltage before adjusting the first magnitude. In one example, the algorithm is configured to adjust the first magnitude using the at least one first control signal. In one example, the algorithm is configured to adjust the first magnitude using the at least one second control signal. In one example, the algorithm is configured to adjust the first magnitude using the at least one first control signal and the at least one second control signal. In one example, the algorithm is configured to initially to set the first magnitude to a maximum value. In one example, the algorithm is configured to use either or both of the at least one first control signal and the at least one second control signal to reduce the first magnitude to the lowest value. In one example, the algorithm is further configured to select at least one of the electrodes as the at least one sensing electrode. In one example, the algorithm is further configured to select at least one of the electrodes as the at least one sensing electrode prior to adjusting the compliance voltage. In one example, the algorithm selects the at least one sensing electrode upon determining that either or both of the following occurs: the tissue current has not reached the first magnitude, or the second magnitude at the at least one input is appropriate for sensing the signals from the patient's tissue. In one example, the algorithm is further configured to modify or suggest a modification to the stimulation program. In one example, the algorithm is further configured to modify or suggest a modification to the stimulation program prior to adjusting the compliance voltage. In one example, the algorithm is configured to continue modifying or suggesting the modification to the stimulation program until determining that either or both of the following occurs: the tissue current has not reached the first magnitude, or the second magnitude at the at least one input is appropriate for sensing the signals from the patient's tissue.

A stimulator device is disclosed having a plurality of electrodes comprising at least one sensing electrode, at least two stimulation electrodes, and at least one common mode electrode. The device may comprise: a sense amp circuit configured to receive at at least one input signals from a patient's tissue at the at least one sensing electrode; tissue driver circuitry configured to provide a common mode voltage to the tissue at the at least one common mode electrode, wherein a tissue current at the common mode electrode is limited to a programmable first magnitude; stimulation circuitry configured to execute a stimulation program to provide a stimulation current of a prescribed amplitude between the at least two stimulation electrodes and through the patient's tissue, wherein the stimulation circuitry is powered by a compliance voltage; either or both of first measurement circuitry configured to generate at least one first control signal indicating whether the tissue current has reached the first magnitude, or second measurement circuitry configured to generate at least one second control signal indicating whether a second magnitude at the at least one input is appropriate for sensing the signals from the patient's tissue; third measurement circuitry configured to generate at least one third control signal indicating whether the stimulation current is provided by the stimulation circuitry at the prescribed amplitude without loading; and control circuitry programmed with an algorithm, wherein the algorithm is configured to use the at least one third control signal and either or both of the at least one first control signal and the at least one second control signal to adjust the compliance voltage.

In one example, the algorithm is configured to adjust the compliance voltage to a lowest value at which the stimulation current is provided by the stimulation circuitry at the prescribed amplitude without loading; and either or both of the following occurs: the tissue current has not reached the first magnitude, or the second magnitude at the at least one input is appropriate for sensing the signals from the patient's tissue. In one example, the algorithm is configured to initially to set the compliance voltage to a maximum voltage. In one example, the algorithm is configured to use the at least one third control signal and either or both of the at least one first control signal and the at least one second control signal to reduce the compliance voltage to the lowest value. In one example, the algorithm is configured to adjust the compliance voltage using the at least one third control signal and the at least one first control signal. In one example, the algorithm is configured to adjust the compliance voltage using the at least one third control signal and the at least one second control signal. In one example, the algorithm is configured to adjust the compliance voltage using the at least one third control signal, the at least one first control signal, and the at least one second control signal. In one example, the algorithm is further configured to use either or both of the at least one first control signal and the at least one second control signal to adjust the first magnitude. In one example, the algorithm is configured to adjust the first magnitude to a lowest value at which either or both of the following occurs: the tissue current has not reached the first magnitude, or the second magnitude at the at least one input is appropriate for sensing the signals from the patient's tissue. In one example, the algorithm is configured to adjust the compliance voltage before adjusting the first magnitude. In one example, the algorithm is configured to adjust the first magnitude using the at least one first control signal. In one example, the algorithm is configured to adjust the first magnitude using the at least one second control signal. In one example, the algorithm is configured to adjust the first magnitude using the at least one first control signal and the at least one second control signal. In one example, the algorithm is configured to initially to set the first magnitude to a maximum value. In one example, the algorithm is configured to use either or both of the at least one first control signal and the at least one second control signal to reduce the first magnitude to the lowest value. In one example, the algorithm is further configured to select at least one of the electrodes as the at least one sensing electrode. In one example, the algorithm is further configured to select at least one of the electrodes as the at least one sensing electrode prior to adjusting the compliance voltage. In one example, the algorithm selects the at least one sensing electrode upon determining that either or both of the following occurs: the tissue current has not reached the first magnitude, or the second magnitude at the at least one input is appropriate for sensing the signals from the patient's tissue. In one example, the algorithm is further configured to modify or suggest a modification to the stimulation program. In one example, the algorithm is further configured to modify or suggest a modification to the stimulation program prior to adjusting the compliance voltage. In one example, the algorithm is configured to continue modifying or suggesting the modification to the stimulation program until determining that either or both of the following occurs: the tissue current has not reached the first magnitude, or the second magnitude at the at least one input is appropriate for sensing the signals from the patient's tissue.

A method is disclosed for operating a stimulator device having a plurality of electrodes comprising at least one sensing electrode, at least two stimulation electrodes, and at least one common mode electrode. The method may comprise: receiving signals from a patient's tissue at the at least one sensing electrode, and providing the received signal to at least one input of a sense amp circuit; providing a common mode voltage to the tissue at the at least one common mode electrode, wherein a tissue current at the common mode electrode is limited to a programmable first magnitude; executing a stimulation program to provide a stimulation current of a prescribed amplitude between the at least two stimulation electrodes and through the patient's tissue using stimulation circuitry powered by a compliance voltage; generating either or both of at least one first control signal indicating whether the tissue current has reached the first magnitude, or at least one second control signal indicating whether a second magnitude at the at least one input is appropriate for sensing the signals from the patient's tissue; and executing an algorithm in the stimulator device, wherein the algorithm is configured to adjust the compliance voltage to a value; and to thereafter use either or both of the at least one first control signal and the at least one second control signal to adjust the first magnitude.

In one example, the method further comprises generating at least one third control signal indicating whether the stimulation current is provided by the stimulation circuitry at the prescribed amplitude without loading. In one example, the algorithm is configured to adjust the compliance voltage using the at least one third control signal. In one example, the algorithm is configured to adjust the compliance voltage to a lowest value at which the stimulation current is provided by the stimulation circuitry at the prescribed amplitude without loading. In one example, the algorithm is further configured to adjust the compliance voltage to a lowest value at which either or both of the following occurs: the tissue current has not reached the first magnitude, or the second magnitude at the at least one input is appropriate for sensing the signals from the patient's tissue. In one example, the algorithm is configured to initially to set the compliance voltage to a maximum voltage. In one example, the algorithm is configured to adjust the compliance voltage using the at least one third control signal and the at least one first control signal. In one example, the algorithm is configured to adjust the compliance voltage using the at least one third control signal and the at least one second control signal. In one example, the algorithm is configured to adjust the compliance voltage using the at least one third control signal, the at least one first control signal, and the at least one second control signal. In one example, the algorithm is configured to adjust the first magnitude to a lowest value at which either or both of the following occurs: the tissue current has not reached the first magnitude, or the second magnitude at the at least one input is appropriate for sensing the signals from the patient's tissue. In one example, the algorithm is configured to adjust the first magnitude using the at least one first control signal. In one example, the algorithm is configured to adjust the first magnitude using the at least one second control signal. In one example, the algorithm is configured to adjust the first magnitude using the at least one first control signal and the at least one second control signal. In one example, the algorithm is configured to initially to set the first magnitude to a maximum value. In one example, the algorithm is configured to use either or both of the at least one first control signal and the at least one second control signal to reduce the first magnitude to the lowest value. In one example, the algorithm is further configured to select at least one of the electrodes as the at least one sensing electrode. In one example, the algorithm is further configured to select at least one of the electrodes as the at least one sensing electrode prior to adjusting the compliance voltage. In one example, the algorithm selects the at least one sensing electrode upon determining that either or both of the following occurs: the tissue current has not reached the first magnitude, or the second magnitude at the at least one input is appropriate for sensing the signals from the patient's tissue. In one example, the algorithm is further configured to modify or suggest a modification to the stimulation program. In one example, the algorithm is further configured to modify or suggest a modification to the stimulation program prior to adjusting the compliance voltage. In one example, the algorithm is configured to continue modifying or suggesting the modification to the stimulation program until determining that either or both of the following occurs the tissue current has not reached the first magnitude, or the second magnitude at the at least one input is appropriate for sensing the signals from the patient's tissue.

A stimulator device is disclosed having a plurality of electrodes comprising at least one sensing electrode, at least two stimulation electrodes, and at least one common mode electrode. The device may comprise: a sense amp circuit configured to receive at at least one input signals from a patient's tissue at the at least one sensing electrode; tissue driver circuitry configured to provide a common mode voltage to the tissue at the at least one common mode electrode, wherein a tissue current at the common mode electrode is limited to a programmable first magnitude; stimulation circuitry configured to execute a stimulation program to provide a stimulation current of a prescribed amplitude between the at least two stimulation electrodes and through the patient's tissue, wherein the stimulation circuitry is powered by a compliance voltage; either or both of first measurement circuitry configured to generate at least one first control signal indicating whether the tissue current has reached the first magnitude, or second measurement circuitry configured to generate at least one second control signal indicating whether a second magnitude at the at least one input is appropriate for sensing the signals from the patient's tissue; and control circuitry programmed with an algorithm, wherein the algorithm is configured to adjust the compliance voltage to a value; and to thereafter use either or both of the at least one first control signal and the at least one second control signal to adjust the first magnitude.

In one example, the device further comprise third measurement circuitry configured to generate at least one third control signal indicating whether the stimulation current is provided by the stimulation circuitry at the prescribed amplitude without loading. In one example, the algorithm is configured to adjust the compliance voltage using the at least one third control signal. In one example, the algorithm is configured to adjust the compliance voltage to a lowest value at which the stimulation current is provided by the stimulation circuitry at the prescribed amplitude without loading. In one example, the algorithm is further configured to adjust the compliance voltage to a lowest value at which either or both of the following occurs: the tissue current has not reached the first magnitude, or the second magnitude at the at least one input is appropriate for sensing the signals from the patient's tissue. In one example, the algorithm is configured to initially to set the compliance voltage to a maximum voltage. In one example, the algorithm is configured to adjust the compliance voltage using the at least one third control signal and the at least one first control signal. In one example, the algorithm is configured to adjust the compliance voltage using the at least one third control signal and the at least one second control signal. In one example, the algorithm is configured to adjust the compliance voltage using the at least one third control signal, the at least one first control signal, and the at least one second control signal. In one example, the algorithm is configured to adjust the first magnitude to a lowest value at which either or both of the following occurs: the tissue current has not reached the first magnitude, or the second magnitude at the at least one input is appropriate for sensing the signals from the patient's tissue. In one example, the algorithm is configured to adjust the first magnitude using the at least one first control signal. In one example, the algorithm is configured to adjust the first magnitude using the at least one second control signal. In one example, wherein the algorithm is configured to adjust the first magnitude using the at least one first control signal and the at least one second control signal. In one example, the algorithm is configured to initially to set the first magnitude to a maximum value. In one example, the algorithm is configured to use either or both of the at least one first control signal and the at least one second control signal to reduce the first magnitude to the lowest value. In one example, the algorithm is further configured to select at least one of the electrodes as the at least one sensing electrode. In one example, the algorithm is further configured to select at least one of the electrodes as the at least one sensing electrode prior to adjusting the compliance voltage. In one example, the algorithm selects the at least one sensing electrode upon determining that either or both of the following occurs: the tissue current has not reached the first magnitude, or the second magnitude at the at least one input is appropriate for sensing the signals from the patient's tissue. In one example, the algorithm is further configured to modify or suggest a modification to the stimulation program. In one example, the algorithm is further configured to modify or suggest a modification to the stimulation program prior to adjusting the compliance voltage. In one example, the algorithm is configured to continue modifying or suggesting the modification to the stimulation program until determining that either or both of the following occurs: the tissue current has not reached the first magnitude, or the second magnitude at the at least one input is appropriate for sensing the signals from the patient's tissue.

BRIEF DESCRIPTION OF THE DRAWINGS

FIGS. 8A and 8B show sense amp circuitry useable in an IPG having sensing capability. Also shown is sensing monitoring circuitry for assessing magnitude of the signals at the inputs to the sensing circuitry.

DETAILED DESCRIPTION

An increasingly interesting development in pulse generator systems is the addition of sensing capability to complement the stimulation that such systems provide. For example, and as explained in U.S. Patent Application Publication 2017/0296823, it can be beneficial to sense a neural response produced by neural tissue that has received stimulation from an IPG. U.S. Patent Application Publication 2017/0296823 shows an example where sensing of neural responses is useful in an SCS context, and in particular discusses the sensing of Evoked Compound Action Potentials, or "ECAPs." U.S. Patent Application Publication 2022/0040486 shows an example where sensing of neural responses is useful in a DBS context, and in particular discusses the sensing of Evoked Resonant Neural Activity, or "ERNA."

Figure 5:
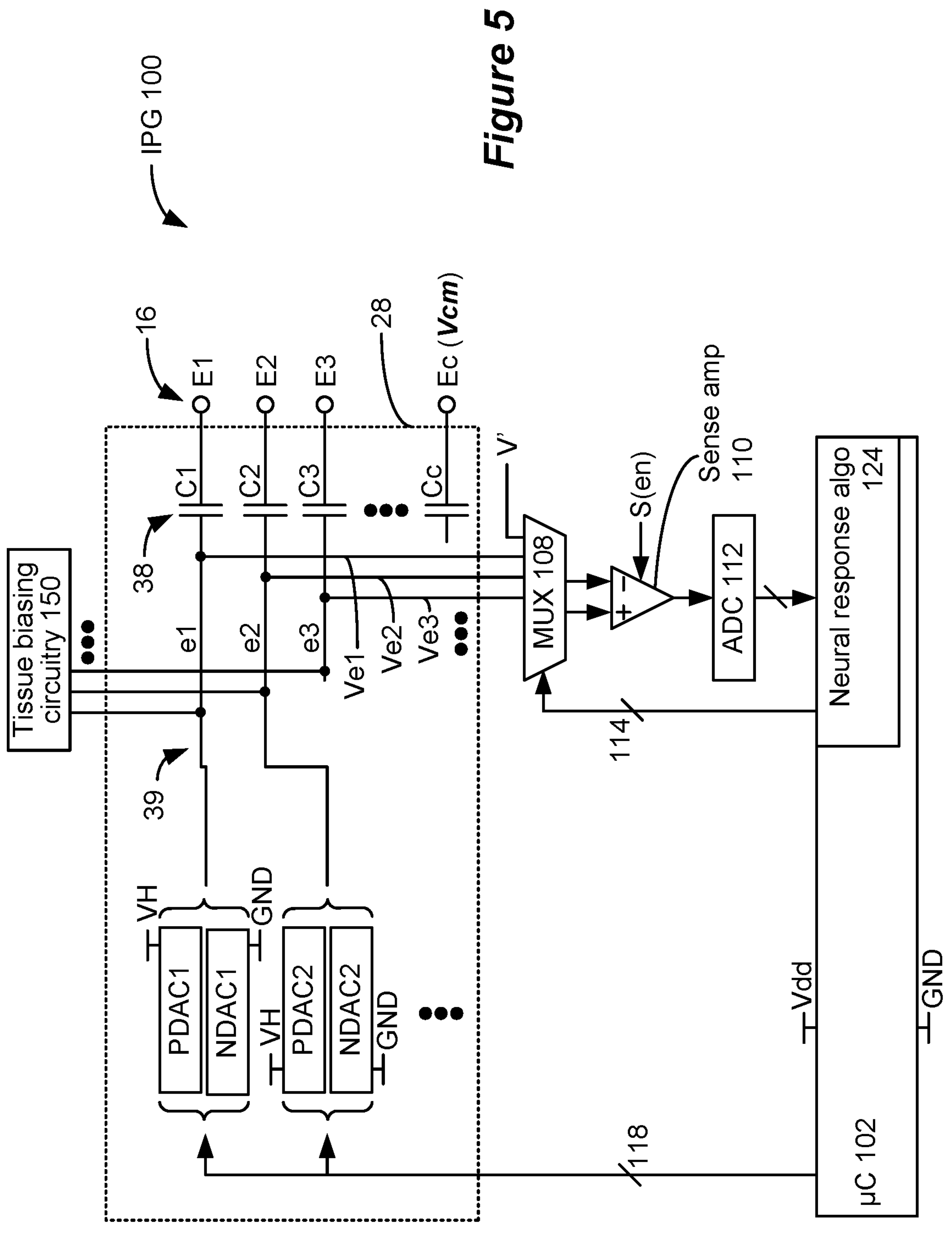
FIG. 5 shows an IPG having neural response sensing capability, and the ability to hold the tissue to a common mode voltage (Vcm) during neural sensing.

FIG. 5 shows basic circuitry for sensing neural responses in an IPG 100. The IPG 100 includes control circuitry 102, which may comprise a microcontroller for example, such as Part Number MSP430, manufactured by Texas Instruments, which is described in data sheets accessible on the Internet. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs) in the IPG 10 as described earlier, which ASIC(s) may additionally include the other circuitry shown in FIG. 5.

FIG. 5 includes the stimulation circuitry 28 described earlier (FIG. 3), including one or more DACs (PDACs and NDACs). A bus 118 provides digital control signals to the DACs to produce currents or voltages of prescribed amplitudes and with the correct timing at the electrodes selected for stimulation. The electrode current paths to the electrodes 16 include the DC-blocking capacitors 38 described earlier.

Figure 4:
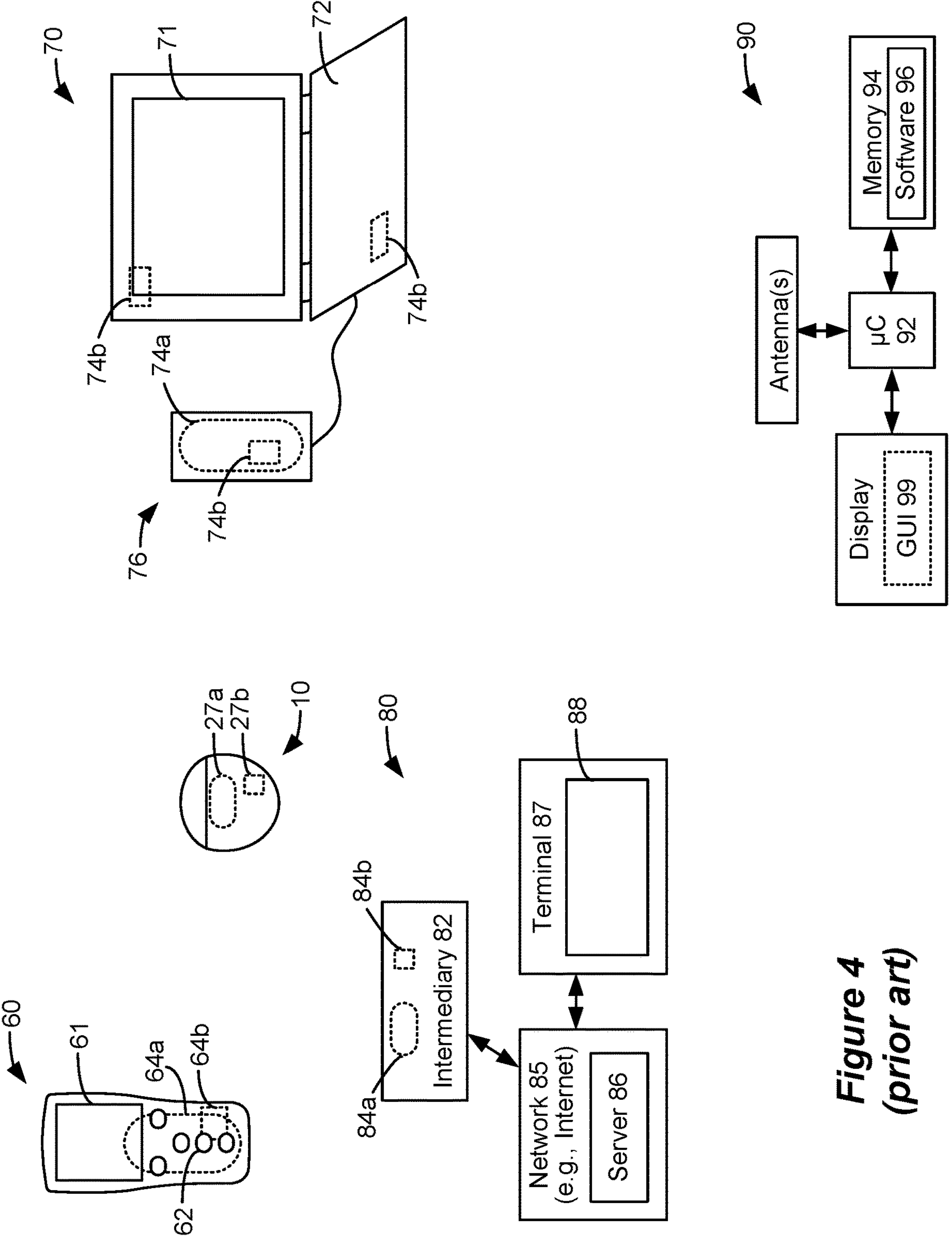
FIG. 4 shows various external systems capable of communicating with and programming stimulation in an IPG, in accordance with the prior art.

FIG. 5 also shows circuitry used to sense neural responses. As shown, the electrode nodes 39 are input to a multiplexer (MUX) 108. The MUX 108 is controlled by a bus 114, which operates to select one or more electrode nodes, and hence to designate corresponding electrodes 16 as sensing electrodes. The sensing electrode(s) selected via bus 114 can be determined automatically by control circuitry 102 and/or a neural response algorithm 124, as described further below. However, the sensing electrode(s) may also be selected by the user (e.g., a clinician) via an external system 60, 70 or 80 (FIG. 4).

Figure 6:
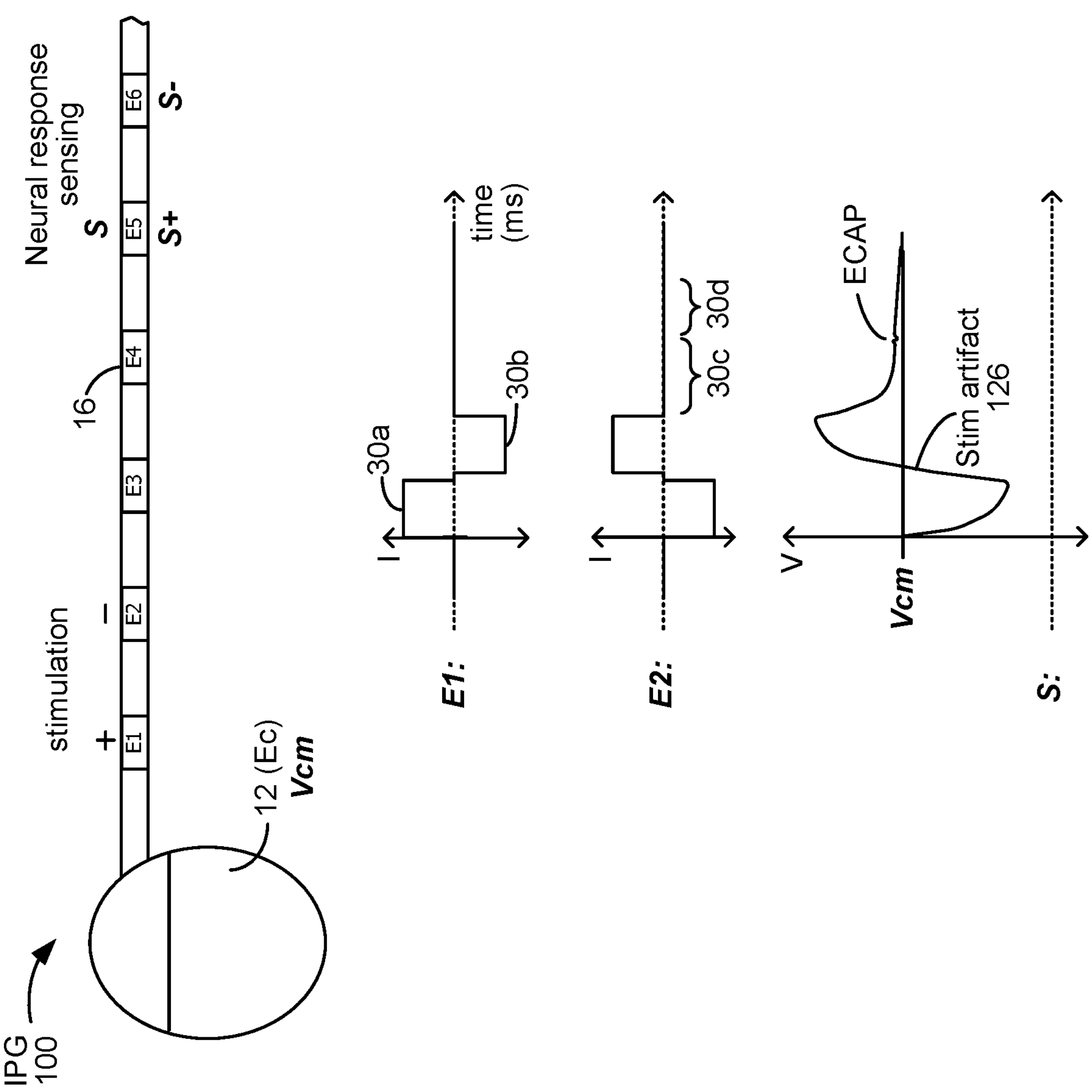
FIG. 6 shows stimulation producing a neural response and a stimulation artifact, and the sensing of that signal at at least one electrode of the IPG.

Electrodes selected as sensing electrodes are provided by the MUX 108 to a sense amplifier circuitry 110, and sensing can occur differentially using two sensing electrodes, or using a single sensing electrode. This is shown in the example of FIG. 6. If single-ended sensing is used, a single electrode (e.g., E5) is selected as a single sensing electrode (S) and is provided to the positive terminal of the sense amp circuitry 110, where it is compared to a reference voltage V' provided to the negative input. The reference voltage V' can comprise any DC voltage produced within the IPG, such as ground, the voltage of the battery (Vbat), or some fraction of the compliance voltage VH (such as VH/2). If differential sensing is used, two electrodes (e.g., E5 and E6) are selected as sensing electrodes (S+ and S−) by the MUX 108, with one electrode (e.g., E5) provided to the positive terminal of the sense amp circuitry 110, and the other (e.g., E6) provided to the negative terminal. Differential sensing can be useful to cancel any common mode voltages present in the tissue and reflected at the electrodes, such as voltages created by the stimulation itself. See, e.g., U.S. Patent Application Publication 2021/0236829.

Although only one sense amp circuit 110 is shown in FIG. 5 for simplicity, there could be more than one, such as a sense amp dedicated to each electrode node. There may also be a plurality of MUXes 108 (e.g., four), each providing their output to a different sense amp circuits 110 (again, four), thus allowing any eight of the electrodes to be selected to act as sensing electrodes at a given time if differential sensing is used. The timing at which sensing occurs can be affected by a sensing enable signal S(en), as discussed further below. Further details of sense amp circuitry 110 are discussed later with reference to FIGS. 8A and 8B.

The analog waveform comprising the sensed neural response and output by the sense amp circuitry 110 is preferably converted to digital signals by an Analog-to-Digital converter (ADC) 112, and input to the IPG's control circuitry 102. The ADC 112 can be included within the control circuitry 102's input stage as well. The control circuitry 102 can be programmed with a neural response algorithm 124 to evaluate the neural responses, and to take appropriate actions as a result. For example, the neural response algorithm 124 may change the stimulation in accordance with the sensed neural response, and can issue new control signals via bus 118 to change operation of the stimulation circuitry 28 to affect better treatment for the patient. The neural response algorithm 124 may also cause the selection of new sensing electrode(s), which can be affected by issuing new control signals on bus 114. Selecting optimal sensing electrode(s) can be important, and may be determined in light of stimulation that is being provided. In this regard, sensing electrodes may be selected near enough to the electrodes providing stimulation (e.g., E1 and E2) to allow for proper neural response sensing, but far enough from the stimulation that the stimulation doesn't substantially interfere with neural response sensing. See, e.g., U.S. Patent Application Publication 2020/0155019.

Neural responses to stimulation are typically small-amplitude AC signals on the order of micro Volts or milliVolts, which can make sensing difficult. The sense amp circuitry 110 needs to be capable of resolving this small signal, and this is particularly difficult when one realizes that this small signal typically rides on a background voltage otherwise present in the tissue. As explained in U.S. Patent Application Publication 2020/0305744, which is incorporated by reference in its entirety, this background voltage can be caused by the stimulation itself. This is shown in the waveforms at the bottom of FIG. 6, which shows the current stimulation pulses, and the signals received at selected sensing electrodes S (including S+ or S−). The sensed signal from the tissue at the sensing electrode(s) includes a neural response—in this case an ECAP—and may also include a stimulation artifact 126 which results from the electromagnetic field that forms in the tissue as a result of the stimulation. Because the DAC circuitry used to provide the stimulation is powered by power supply voltages VH and ground (see FIG. 3), the stimulation artifact 126 will vary between these voltages, and can comprise several Volts.

Differential sensing using two sensing electrode S+ and S− is useful because it allows the sense amp circuitry 110 to subtract any common mode voltages like the stimulation artifact 126 present in the tissue, hence making the neural response easier to resolve. However, this will not remove the stimulation artifact 126 completely, because the stimulation artifact 126 will not be exactly the same at each sensing electrode. Therefore, even when using differential sensing, it may be difficult to resolve the small signal neural response which may still ride on a significant background voltage.

That being said, the stimulation artifact 126 is not always a detriment to sensing. In fact, sometimes it is useful to sense stimulation artifacts 126 in their own right, because like neural responses they can also provide information relevant to adjusting a patient's stimulation, or to automatically selecting a best combination of sensing electrodes. See, e.g., U.S. Patent Application Publications 2020/0251899 and 2021/0236829.

U.S. Pat. No. 11,040,202, which is incorporated herein by reference in its entirety, describes tissue biasing circuitry 150 that assists in neural response sensing by holding the tissue to a common mode voltage, Vcm, via a capacitor (such as one of the DC-blocking caps 38). Preferably, this common mode voltage Vcm is approximately equal to half the compliance voltage, i.e., ~VH/2, as discussed further below. When a common mode voltage Vcm is provided to the tissue, AC signals present in the tissue (neural responses, any stimulation artifacts) will also be referenced to this voltage. This is a helpful improvement, because it tends to stabilize the DC level of the signals being input to the sense amp circuitry 110 by the sensing electrodes.

The common mode voltage Vcm is preferably established in the tissue at the conductive case electrode Ec. The case electrode Ec is relatively large in area and thus low in resistance. A patient's tissue is also of relatively low resistance, and therefore the case electrode Ec comprises a suitable means for establishing Vcm for the whole of the tissue even if it is implanted at a distance from the lead-based electrodes 16 used for stimulation and sensing. That being said, one or more of the lead-based electrodes could also be used to provide Vcm, as explained in further detail in U.S. patent application Publication 2023/0138443, which is incorporated herein by reference in its entirety. For example, if the case electrode Ec is being used to actively drive a therapeutic stimulation current (e.g., monopolar stimulation), it would be necessary to use a lead-based electrode to provide Vcm to the tissue. It is assumed for simplicity in this disclosure that the case electrode Ec is used to provide Vcm to the tissue to assist with sensing.

Figure 7A:
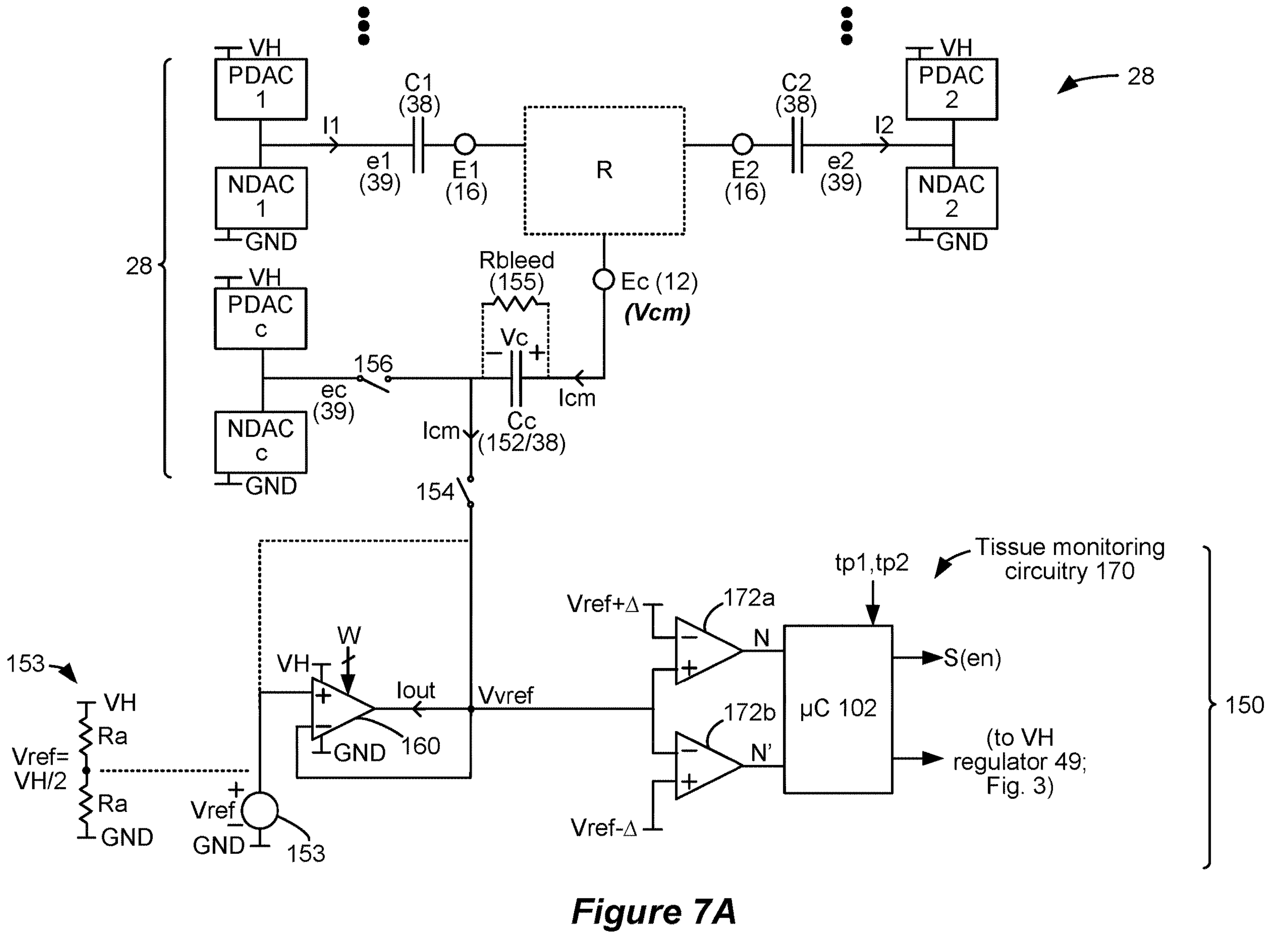
FIGS. 7A and 7B show tissue biasing circuitry used to provide a common mode voltage (Vcm) to the patient's tissue through one or more of the electrodes, as is useful when sensing signals from the tissue. Also shown is tissue monitoring circuitry for assessing or adjusting the drive strength of the tissue driver in the tissue biasing circuitry.
Figure 7B:
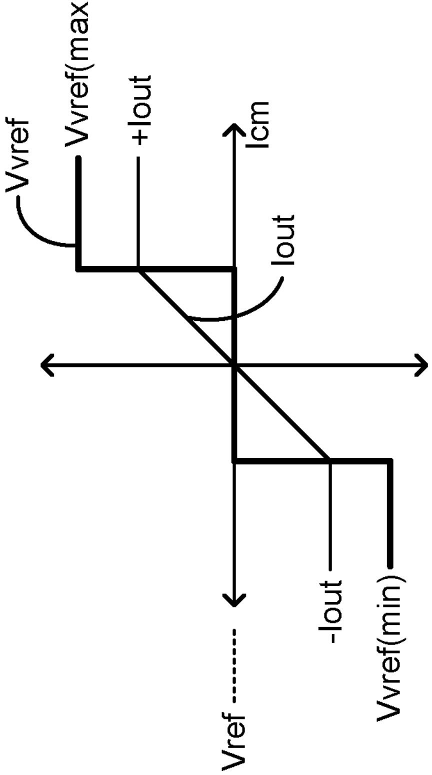

FIGS. 7A and 7B show details of the tissue biasing circuitry 150 use to provide Vcm to the tissue at a selected common mode electrode (e.g., Ec). FIG. 7A also shows portions of the stimulation circuitry 28 associated with selected stimulation electrodes E1 and E2 and with the common mode electrode Ec.

The tissue biasing circuitry 150 passively biases the case electrode Ec to Vcm using a capacitor Cc 152/38 and a voltage source 153 inside the case 12. In the example shown in FIG. 7A, the capacitor Cc 152/38 serves a dual function: its acts as a common mode capacitance to assist in setting Vcm at the case electrode Ec when tissue biasing circuitry 150 is active, and also acts as a DC blocking capacitor (see 38, FIG. 3) when the case electrode Ec is actively driven (during monopolar stimulation) using the stimulation circuitry 28 (using PDACc and/or NDACc). Switches 156 and 154 can facilitate these different uses of the case electrode Ec. When the stimulation circuitry 28 is used to drive the case electrode Ec, switch 156 is closed to couple the relevant DAC circuitry (PDACc and NDACc) to Cc 152/38, and switch 154 is opened to disconnect the tissue biasing circuitry 150. By contrast, when the tissue biasing circuitry 150 is used to passively form Vcm at the case electrode Ec, switch 154 is closed, and switch 156 is opened to disconnect the stimulation circuitry 28. Additional switches 154 may be used to connect the tissue biasing circuitry 150 to other of the electrodes to allow them to provide Vcm to the tissue, but again this detail isn't shown.

Figure 3:
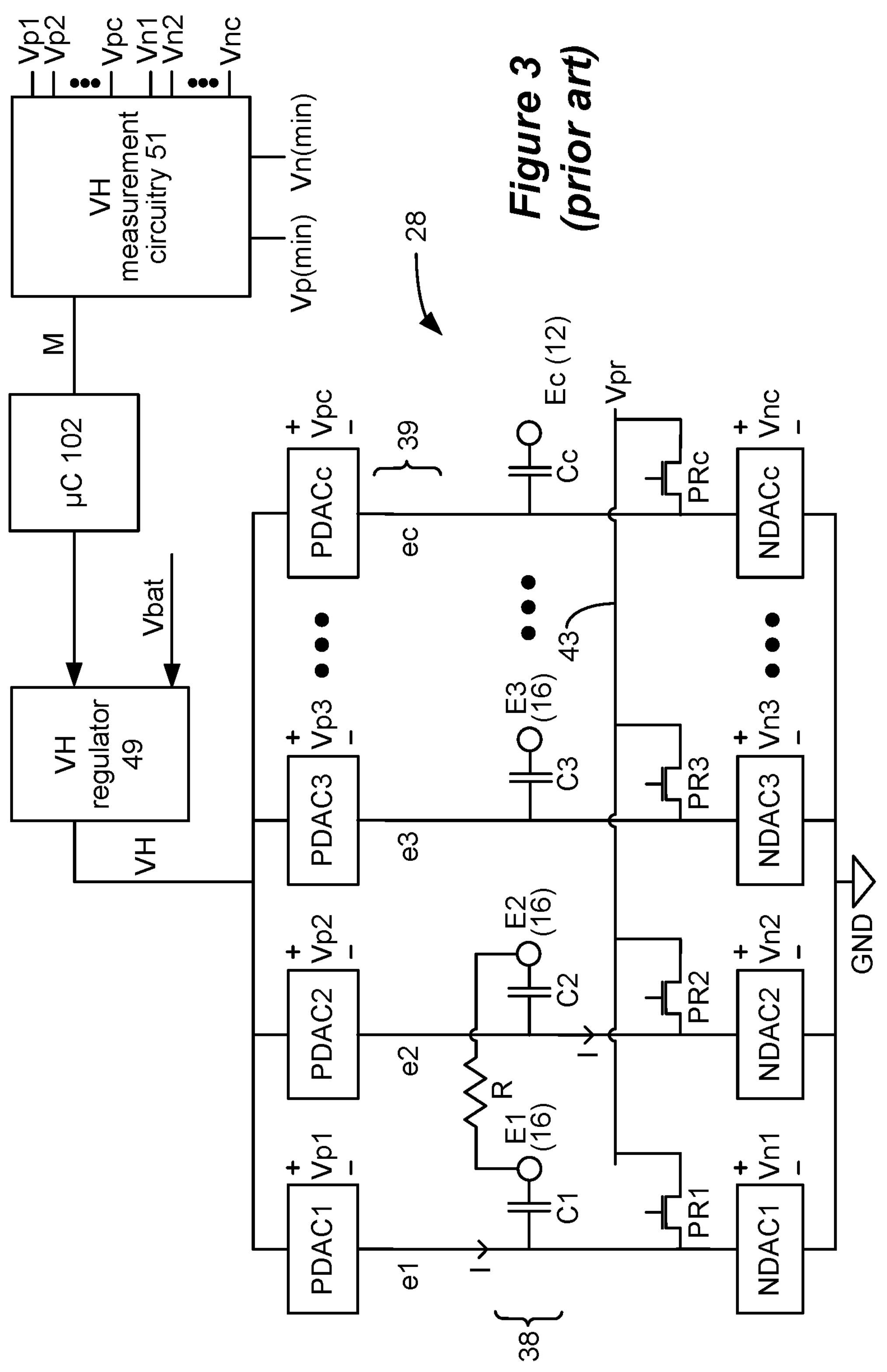
FIG. 3 shows stimulation circuitry useable in the IPG, in accordance with the prior art, including circuitry for assessing and adjusting a compliance voltage used to power the stimulation circuitry.

The voltage source 153 produces a reference voltage Vref, which may be adjustable. Vref preferably has a value between ground (0V) and the compliance voltage (VH), or is equal to these values. Vref may also have a value that varies as a function of the compliance voltage VH, which as noted earlier may vary by operation of VH regulator 49 (FIG. 3). Most preferably, and as assumed from this point forward, Vref may be set to VH/2, and hence may vary as VH varies. A voltage source 153 producing Vref=VH/2 as shown in FIG. 7A may be formed as a VH voltage divider comprising high-resistance resistors Ra and Rb each having the same high value, although other generator circuits could be used to form Vref as well.

Figures 1, 2A, 2B:
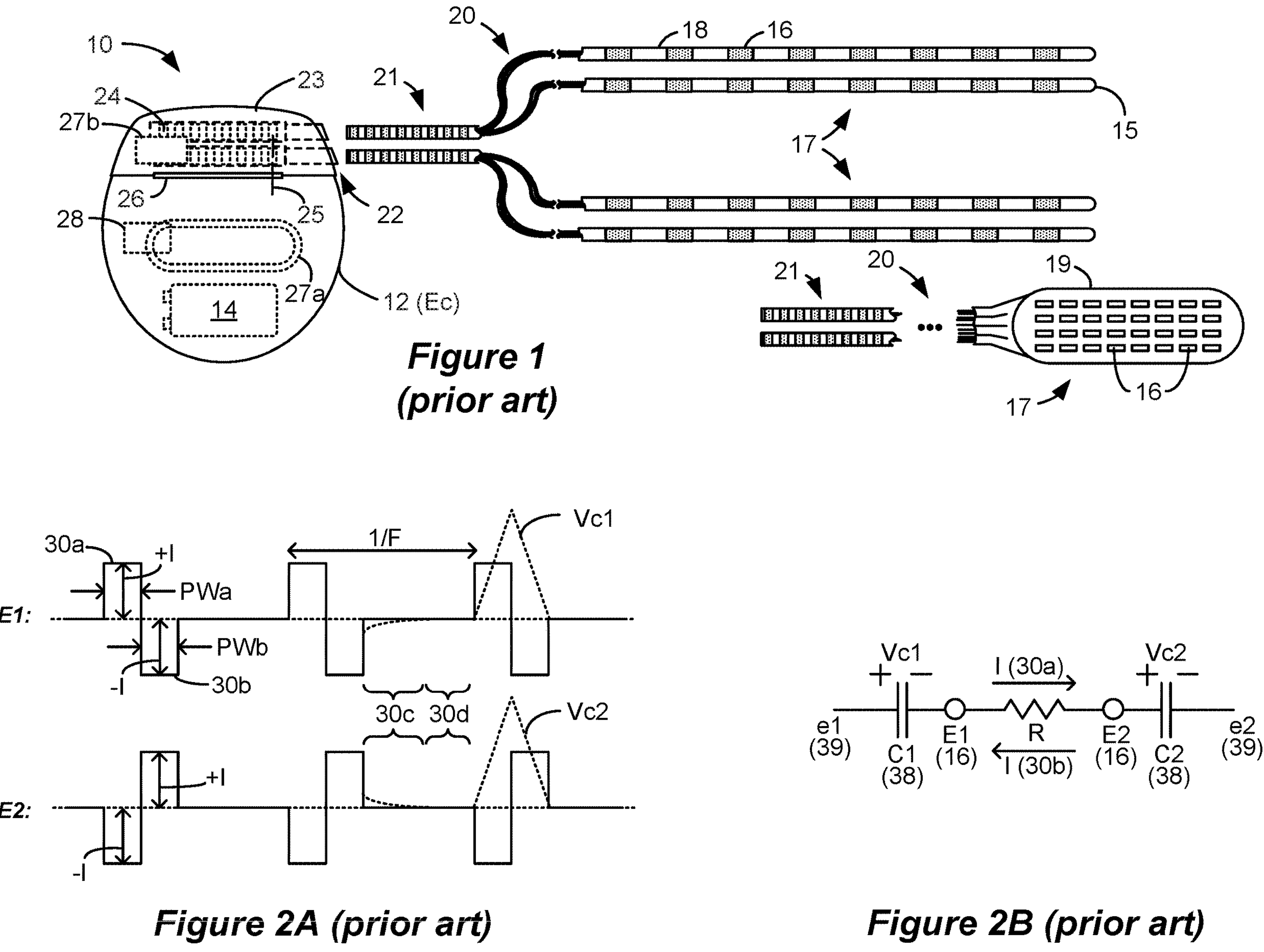
FIG. 1 shows an Implantable Pulse Generator (IPG), in accordance with the prior art.
FIGS. 2A and 2B show an example of stimulation pulses producible by the IPG, in accordance with the prior art.

The common mode voltage Vcm established in the tissue R at the case electrode Ec comprises the sum of Vref (or Vvref as discussed further below) and any voltage formed across capacitor Cc 152/38 (Vc). As explained in the '202 patent, Vc can form when a current Icm flows to the case electrode Ec, such as when the stimulation currents issued by the stimulation circuitry 28 are imbalanced. Consider the example in FIG. 7A, where an anodic current I1 is being sourced to the tissue R through electrode E1, and a cathodic current I2 is being sunk from the tissue through electrode E2. (FIG. 2A, first phase 30*a*). Normally, these currents I1 and I2 would be programmed (at PDAC1 and NDAC2) to have the same value. Icm would therefore be zero, meaning capacitor Cc 152/38 would not charge (Vc=0); the common mode voltage Vcm would therefore be set to Vref=VH/2 (or Vvref) at the case electrode Ec.

However, these currents I1 and I2 may be slightly imbalanced, particularly if the PDACs are operating more strongly than the NDACs, or vice versa. If |I1|>|I2|, Icm would be positive, causing Vc to increase over time, which sets Vcm>Vref. If |I1|<|I2|, Icm would be negative, causing Vc to decrease over time, which sets Vcm<Vref. As such, Vcm is pseudo constant, but is generally established at ~VH/2. Once Vcm is established at the case electrode Ec and hence in the tissue R, voltages otherwise formed in the tissue, such as those accompanying the production of stimulation pulses, will be established relative to Vcm. This can ease sensing of small signals in the tissue at the sense amp 110, such as the neural responses explained above.

FIG. 7A also shows an optional bleed resistor Rbleed 155 included in parallel with the capacitor Cc 152/38. The bleed resistor Rbleed 155 is preferably of a high resistance (e.g., 1 MegaOhm or higher), and allows charge to bleed slowly off the capacitor Cc 152/38, for example, during periods when the tissue biasing circuitry 150 is not being used. Rbleed is discussed further in the '202 patent and the '443 Publication incorporated above.

The above-incorporated '202 patent discloses other optional circuitry that can be included in the tissue biasing circuitry 150. For example, circuitry 150 can include an amplifier 160. Amplifier 160 is preferably an operational transconductance amplifier (OTA), which produces a virtual reference Vvref on the bottom plate of capacitor Cc 152/38. The OTA 160 is programmable via control signals W to set a maximum output current for the OTA. More specifically, W constrains the output current between +out and −Iout. Limiting the output of the OTA 160 to +/−|Iout| limits Icm, limits the current to the electrode that has been designated to provide Vcm to the tissue (in this case, the case electrode Ec). Limiting Icm minimizes inadvertent, unprescribed stimulation to the tissue, which might otherwise negatively affect stimulation therapy prescribed at the selected stimulation electrodes. Note that use of OTA 160 is not strictly required, and instead the voltage source 153's output Vref (e.g., VH/2) can be connected (e.g., via switch 154) to the bottom plate of capacitor Cc 152/38, as shown in the dotted lines in FIG. 7A (in which case Vvref simply equals Vref).

OTA 160 is preferably configured as a follower, in which the virtual reference voltage Vvref is fed back to the negative input of the OTA. The positive input of the OTA 160 is provided with reference voltage Vref provided by voltage source 153, which again is preferably set at VH/2. When connected as a follower, the OTA 160's output Vvref will equal Vref so long as Icm is between −Iout and +Iout, as shown in FIG. 7B. Given the polarity with which Iout is defined in FIG. 7A, Iout=Icm so long as Icm is between-Iout and +Iout.

If Icm exceeds +Iout or is less than-out, perhaps because currents I1 and I2 are significantly imbalanced, then the OTA 160 will limit Icm to +Iout or −Iout respectively. Because the OTA 160 cannot accommodate the excess current is these situations, Vvref will be pulled away from Vref to values Vvref (max) or Vvref (min), as shown in FIG. 7B. Capacitor Cc 152/38 will then start to charge in a current-limited fashion (with Icm=+Iout or −Iout), causing Vcm to increase or decrease, and Vvref to decrease or increase. As the capacitor Cc continues to charge upon the issuance of subsequent pulses, Vcm will continue to rise or fall, and Vvref will continue to fall or rise, until a steady state is reached. The OTA 160 and associated circuitry for providing Vcm to the tissue comprises "tissue driver circuitry," with a drive strength (+/−|Iout|) that is adjustable (per control signals W).

Still other optional circuitry within tissue biasing circuitry 150 is shown in FIG. 7A, including tissue monitoring circuitry 170. Again, this circuitry 170 is discussed in detail in the above-incorporated '202 patent, and is only briefly summarized here. Tissue monitoring circuitry 170 receives the virtual reference Vvref as an input, from which a couple of things can be determined. First, monitoring Vvref allows the control circuitry 102 in the IPG 10 to decide when neural response sensing is best performed in the IPG 10, i.e., when the sensing enable signal S(en) should be asserted to enable the sense amp circuitry 110 (see FIG. 5). Second, monitoring Vvref is also useful in determining whether the compliance voltage VH should be adjusted at the VH regulator 49 (FIG. 3).

Both of these determinations depend on how significantly the virtual reference Vvref varies from the reference voltage Vref (e.g., VH/2) output by the voltage source 153. In this regard, Vvref is input to a window comparator formed from comparators 172*a* and 172*b*, which sets a voltage window from Vref+Δ to Vref−Δ (where Δ may equal 100 mV for example). If Vvref is higher than Vref+Δ, signal Nis asserted. If Vvref is lower than Vref−Δ, signal N' is asserted. The control circuitry 102 in the IPG 100 can assess N and N' in conjunction with timing control signals tp1 or tp2 that indicate whether stimulation is occurring during the first or second of pulse phases 30*a* and 30*b*. As explained in the '202 patent, sensing enable signal S(en) is asserted only when control signals N' and N are not asserted, meaning that Vvref is between Vref+Δ and Vref−Δ.

The tissue monitoring circuitry 170 can also inform whether the compliance voltage VH should be adjusted. For example, and as discussed in the '202 patent, if only N is asserted during one phase pulse phase (e.g., 30*a*), and if only N' is asserted during the other phase (e.g., 30*b*), then the control circuitry 102 may signal the VH regulator 49 to increase VH.

Figure 8A:
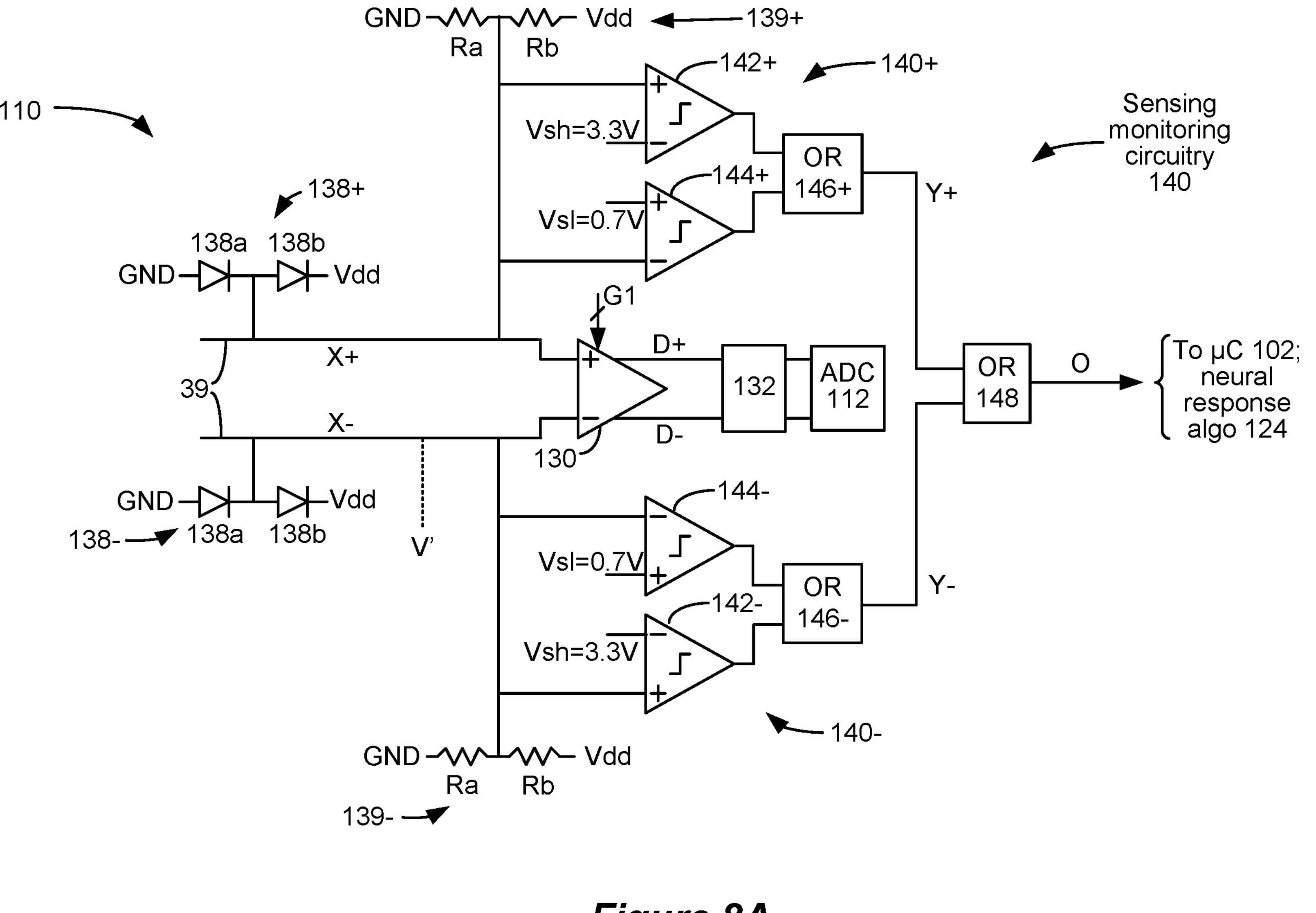

FIGS. 8A and 8B show further details of the sense amp circuit 110, which includes sensing monitoring circuitry 140. Many of the details shown in FIG. 8A are discussed in detail in U.S. Patent Application Publication 2020/0305744. Because the reader is assumed familiar with the '744 Publication, sense amp circuitry 110 and sensing monitoring circuitry 140 are only briefly summarized here.

As discussed earlier, the sense amp circuit 110 includes a differential amplifier (diff amp) 130 which receives input signals X+ and X+ from the electrode nodes of the selected sensing electrodes S+ and S−, and which provides a differential output to analog outputs D+ and D−. Diff amp 130 is assumed in this example to comprise a low-voltage diff amp powered by Vdd, which is assumed to equal 3.3 V, although this value could vary. However, a high-voltage diff amp powered by VH could be used as well. Furthermore, both low-voltage (Vdd) and high-voltage (VH) diff amps can be used, thus allowing the control circuitry to select the use of either diff amp under different circumstances, as discussed in U.S. Patent Application Publication 2023/0173273, which is incorporated herein by reference in its entirety. Diff amp 130 may be used in a well-known chopper amplifier configuration, as explained in the '273 Publication, although this detail isn't shown here. Sense amp circuit 110 can also include DC offset compensation circuitry designed to equilibrate the DC voltage levels at the inputs X+ and X−, as also explained in the '273 Publication, but again this detail isn't shown. The specific circuitry used for diff amp 130 can vary, but a simple example is shown in FIG. 8B. Preferably the gain of the diff amp 130 is programmable using control signals G1 issued by the control circuitry 102.

The differential analog output D+ and D− can be further processed by analog processing circuitry 132 before being digitized by the ADC 112, as shown in FIG. 8B. Such processing circuitry 132 is described further in the above-incorporated '273 Publication.

The sense amp circuitry 110 of FIGS. 8A and 8B is shown assuming that differential sensing is employed using two selected sensing electrodes (S+ and S−). However, one skilled will understand that the circuitry could be modified for single-ended sensing using only one sensing electrode(S) and one input (X+) as well. As shown in dotted lines in FIG. 7, one of the inputs (e.g., X−) can be provided with a fixed reference voltage V' as discussed earlier (see FIG. 5).

Referring again to FIG. 8A, to prevent damage to or improper operation of the diff amp 130, inputs X+ and X− are provided with clamping circuits 138+ and 138− respectively. These circuits prevent the voltage on inputs X+ and X− from exceeding voltages close to Vdd (e.g., 3.3V) and from falling below voltages close to ground, which protects the input of the diff amp 130. Inputs X+ and X− are also connected to DC-level shifting circuits 139+ and 139−, to reference to inputs to a DC voltage consistent with the input requirements for the diff amp 130, such as ½Vdd. Clamping circuits 138+ and 138−, and DC-level shifting circuits 139+ and 139−, are discussed in further detail in the '744 Publication.

Also connected to inputs X+ and X− is the sensing monitoring circuitry 140, which operates to issue a signal O dependent on the magnitudes of the signals at the inputs. This sensing monitoring circuitry 140 is shown split into two pieces: 140+ for assessing the voltage on input X+, and 140− for assessing the voltage on input X−. However, in a single-ended sensing approach in which one of the inputs (e.g., X−) is held to a DC reference voltage (V'), only one of these pieces (e.g., 140+) would be required. Circuits 140+ and 140− are similar, and 140+ is briefly discussed.

Circuitry 140+ includes comparators 144+ and 142+ which together comprise a window comparator to determine whether input X+ is between a low sense reference voltage Vsl and a high sense reference voltage Vsh. These references voltages Vsl and Vsh can be set by regulator circuitry as disclosed in the '744 Publication, and are set to values appropriate for proper diff amp 130 operation. Here it is assumed that Vsl is equal to the threshold voltage Vtt (e.g., 0.7V) at which the input transistors in the diff amp 130 will start to draw a currents (FIG. 8B, I+ and I−), while Vsh is equal to the power supply voltage that powers the diff amp 130 (e.g., Vdd=3.3V). If the magnitude of input X+ is between these voltages Vsl and Vsh, and hence at a magnitude suitable for diff amp 130 operation, both of comparators 142+ and 144+ output a '0'. If X+ is below 0.7V, i.e., too low to drive a current I+ in the diff amp 130, comparator 144+ outputs a '1'. If X+ is above 3.3V, i.e., too high for the diff amp 130 because current I+ would saturate, comparator 142+ outputs a '1'. These outputs can be logically ORed together at an OR gate 146+ to provide an output Y+ indicative of whether input X+ is at a magnitude for proper diff amp 130 operation (Y+='0' if 0.7V<X+<3.3V), or not (Y+='1' otherwise).

Circuitry 140− is essentially the same, but indicates at output Y− whether input X− is at a suitable level (Y−='0') for proper diff amp 130 operation. Outputs Y+ and Y− can be logically ORed by OR gate 148 to generate the signal O described earlier, thus setting O='0' if both of inputs X+ and X− are at proper magnitudes for diff amp operation 130, and setting O='1' if either or both of inputs X+ and X− are at a magnitude unsuitable for proper diff amp operation 130. Signal O can be used in different useful manners. For example, as disclosed in the '744 Publication, signal O can be sent to the neural response algorithm 124 in the control circuitry 102 to inform whether the data as output by the diff amp 130 is valid at a given time. Also, as disclosed in the above-incorporated '273 Publication, signal O can be used to select between the use of low- or high-voltage diff amps in IPG designs having both types of amplifiers available.

Note that sensing monitoring circuitry 140 can be associated with or comprise part of control circuitry 102. For example, analog-to-digital converters can sample and produce digital representations of inputs signals X+ and X−. These digital representations can be assessed and compared to thresholds (Vsl, Vsh) digitally to determine signal O. In other words, sensing monitoring circuitry 140 can be implemented using digital logic, and analog comparators circuits (142, 144) may not be necessary.

Figure 9A:
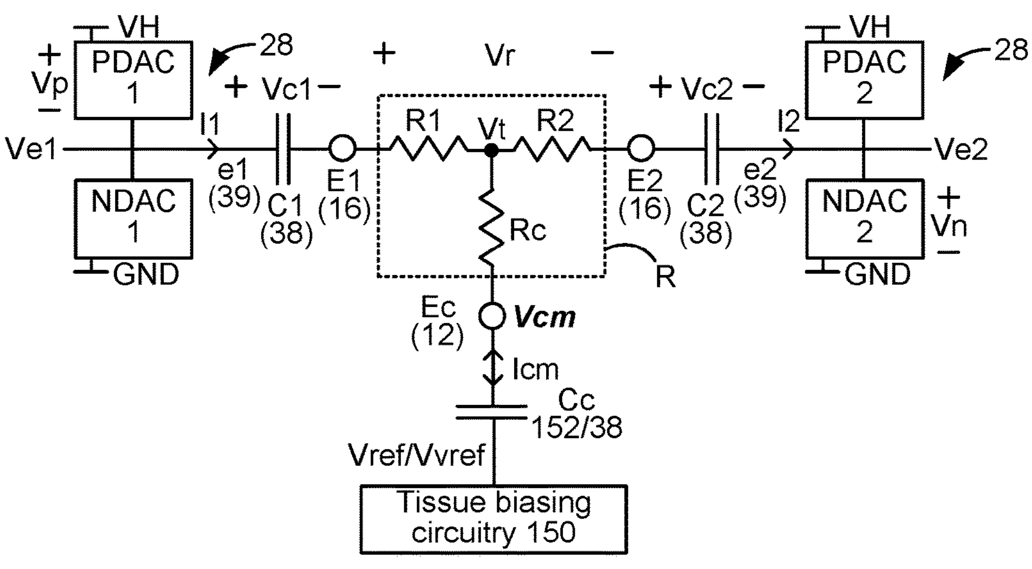
FIGS. 9A and 9B show the voltages in the tissue and at the active electrodes. More specifically, these figures show how these voltages are affected when a common mode voltage Vcm is provided to the tissue, and when current or resistance imbalances are present, and the effect that such variables have on the compliance voltage VH.
Figure 9A:
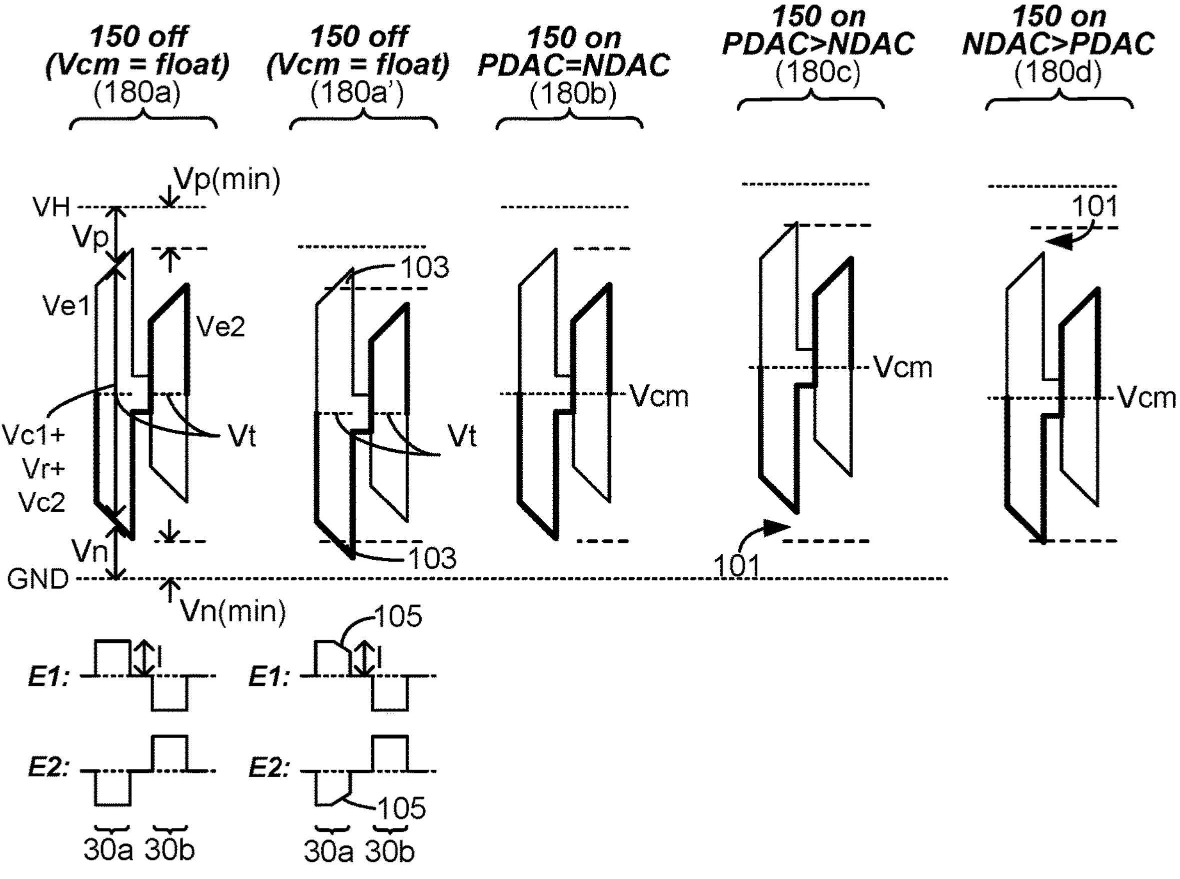
Figure 9B:
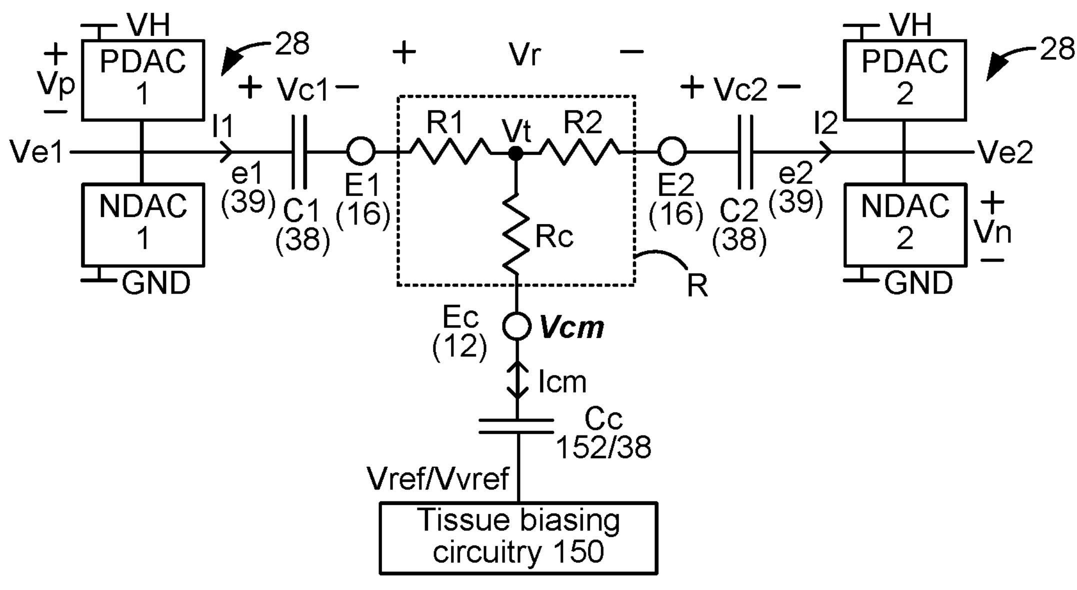
Figure 9B:
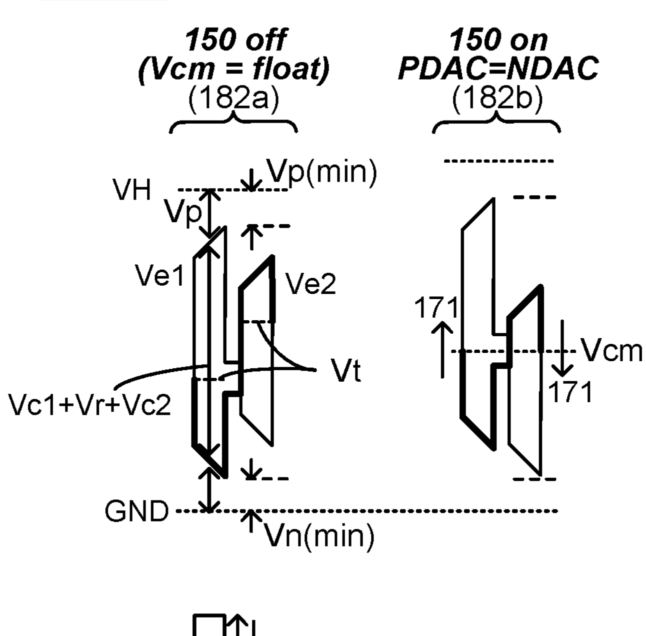
Figure 9B:
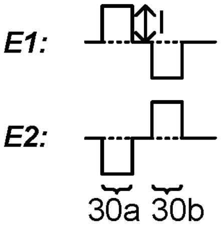

FIGS. 9A and 9B illustrate issues related to setting the compliance voltage VH that provides power to (among other circuits) the stimulation circuitry 28, in particular when tissue biasing circuitry 150 is used to hold the tissue to a common mode voltage Vcm. These figures again show use of the case electrode Ec 12 to provide Vcm to the tissue, although as mentioned earlier any other electrode including one or more of the leads-based electrodes could be used to provide Vcm instead. These figures also assume that a biphasic constant current pulse with pulse phases 30*a* and 30*b* is issued between electrodes E1 and E2 to provide a stimulation current through the tissue R as in earlier examples, although again other electrodes could have been selected to provide the stimulation current. Notice further that the resistance of the tissue R is modeled as a network of resistances R1, R2, and Rc connected to electrodes E1, E2, and Ec respectively. Such modelling is useful to consider, because the resistance between each selected electrode E1 and E2 and the case electrode Ec may not be the same, which is not surprising given the complex tissue environment and distance between electrodes E1 and E2 and the case electrode Ec. Although this network is shown using resistances for convenience, one skilled in the art will understand that this network may also be expressed with complex impedances inclusive of capacitance and other non-linear effects. ("Resistance" as used herein should be understood to include complex impedances more generally). A node Vt in the middle of this network can be understood as generally indicative of the voltage in the tissue.

As discussed in the above-incorporated '202 patent, providing Vcm to the tissue impacts the value to which the compliance voltage VH should be set, and this is explained with reference to the waveforms in FIGS. 9A and 9B. These waveforms show the voltages that are formed at the electrode nodes 39 e1 and e2 (Ve1 and Ve2) under various conditions when producing a biphasic current pulse, with Ve2 shown with a darker line than Ve1 so that these voltages can be differentiated. The electrode node voltages Ve1 and Ve2 are shown with reference to the compliance voltage VH used to power the stimulation circuitry 28. All relevant voltage drops are shown, including the voltage drops across the tissue (Vr), the DC-blocking capacitors 39 (Vc1 and Vc2), and the active PDACs and NDACs (Vp and Vn). As shown, Ve1 is initially higher than Ve2 because of the direction that the current is flowing during the first pulse phase 30*a*. Ve1 will increase and Ve2 will decrease during the first pulse phase 30*a* as the DC-blocking capacitors 38 charge (Vc1, Vc2). This also causes the voltage drops across the active PDAC (PDAC1; Vp) and NDAC (NDAC1; Vn) to decrease. During the second pulse phase 30*b*, the polarity of the current is reversed, and so Ve2 is now higher than Ve1. The voltages Vc1 and Vc2 decrease during the second pulse phase 30*b* as their stored charge is recovered, which causes Ve1 to decrease and Ve2 to increase, while Vp and Vn (now across PDAC2 and NDAC1) decrease.

FIGS. 9A and 9B also show the minimum drops that are permissible across the active PDAC circuitry (Vp(min)) and NDAC circuitry (Vn(min)) used to form the programmed current, and which are used by the VH measurement circuitry 51 (FIG. 3) when deciding whether the compliance voltage VH should be adjusted.

In FIG. 9A, it is assumed that R1 equals R2 in the tissue model. Waveform 180*a* shows the electrode node voltages Ve1 and Ve2 when tissue biasing circuitry 150 is not used (e.g., switch 154 in FIG. 7A is opened, and Vcm at the case electrodes floats). Voltage Vt within the resistance model—indicative of the tissue voltage—floats to whatever level would otherwise be indicated by the stimulation. In the case where the resistances are balanced, it is seen that Vt is the same during each of the pulse phases 30*a* and 30*b*. Assuming Vp(min) and Vn(min) are equal, Vt would be approximately VH/2. Further, VH regulator circuitry 49 (FIG. 3) operates to adjust the compliance voltage VH such that Ve1 and Ve2 would be generally be tightly pinned within Vn(min) and VH−Vp(min) without loading of the current pulses, thus keeping the voltage drops across the active DAC circuitry (in particular Vp1 across PDAC1 and Vn2 across NDAC2 in FIG. 3) above their minimum values Vp(min) and Vn(min), which establishes VH at a suitably high and energy-efficient level.

Loading of the current pulses is shown with reference to waveform 180*a*'. Here, the compliance voltage VH is not high enough (perhaps because the VH measurement circuitry 51 and regulator circuitry 49 have not yet had time to act to adjust VH), and thus Ve1 and Ve2 breach Vn(min) and VH-Vp(min) during times 103 for at least a portion of the current pulses. This means that the voltage drops across the DAC circuitry (e.g., Vp1 and Vn2) are too low, i.e., less than Vp(min) and Vn(min). This causes the current pulses to become loaded 105 during such times, meaning the currents are lower than prescribed (+/−I). Note that loading of the current pulses can occur in either phase 30*a* or 30*b*, and at only one of the electrodes, depending on the circumstances.

For waveforms 180*b*-180*d*, tissue biasing circuitry 150 is used (e.g., switch 154 is closed), and thus a common mode voltage Vcm is formed in the tissue. Ve1 and Ve2 become referenced to Vcm during each of pulse phases 30*a* and 30*b*.

In waveform 180*b*, it is assumed that the currents from the DAC circuitry are balanced, with the PDACs and NDAC providing currents of the same magnitude. Icm would equal zero, and Vcm is thus established at approximately VH/2 (Vref), just as occurred in waveform 180*a*.

In waveform 180*c*, it is assumed initially that the currents from the DAC circuitry are mismatched, with the PDACs providing slightly larger currents that the NDACs. Icm would initially be positive, which eventually drives Vcm higher, and Ve1 and Ve2 (referenced to Vcm) higher. This may cause Ve1 to eventually surpass VH−Vp(min). Therefore, in this example, VH measurement circuitry 51 causes VH regulator 49 to increase VH to alleviate this problem. Note that increasing the compliance voltage VH also (further) increases Vcm in this example, because Vref (=VH/2) will also increase.

In waveform 180*d*, it is assumed initially that the currents are again mismatched, with the NDACs providing slightly larger currents that the PDACs. Icm would initially be negative, eventually driving Vcm, Ve1, and Ve2 lower. This may cause Ve2 to become lower than Vn(min). Again, VH measurement circuitry 51 and VH regulator 49 will raise VH to alleviate this problem. Raising VH increases Vref (=VH/2), and hence Vcm, Ve1 and Ve2, until Ve2 is just barely below Vn(min) as shown in waveform 180*d*. Even though the tendency would be for Vcm to decrease (Icm<0), raising VH also raises Vref, which counteracts to raise Vcm.

A comparison of waveforms 180*c* and 180*d* to waveform 180*b* in FIG. 9A shows that use of the tissue biasing circuitry 150 may warrant increasing the value of the compliance voltage VH if the currents provided by the PDAC(s) and NDAC(s) are not balanced. Increasing the compliance voltage is generally not preferred as this draws extra power in the IPG 100, and will more quickly drain the IPG's battery 14 (FIG. 1). In particular, extra headroom 101 is provided, during which the voltage drops Vn across the NDACs (waveform 180*c*) and the voltage drops Vp across the PDACs (waveform 180*d*) are larger than required. However, this downside is offset by the benefit that a controlled common mode Vcm provides when sensing neural responses in the tissue, while still ensuring that the current pulses are formed at the selected stimulation electrodes without loading.

In FIG. 9B, it is assumed that R1 is greater than R2 in the tissue model, which also impacts the compliance voltage VH. Waveform 182*a* assumes that tissue biasing circuitry 150 is not used, and thus tissue voltage Vt floats to whatever level would otherwise be indicated by the stimulation. In this case, it is seen that Vt is different during pulse phases 30*a* and 30*b*: Vt is lower during pulse phase 30*a* because more voltage is dropped across R1 than R2; and Vt is higher during pulse phase 30*b* when the polarity of the current is reversed. VH would however still be established by the VH measurement circuitry 51 and the VH regulator 49 at the same value as when the resistances were balanced, as shown in waveform 180*a* of FIG. 9A.

For waveform 182*b*, tissue biasing circuitry 150 is used (e.g., switch 154 is closed), and thus Vcm is formed in the tissue. Ve1 and Ve2 are referenced to Vcm during each of pulse phases 30*a* and 30*b*, which in this example causes the waveforms to shift 171 during each of the pulse phases because of the resistance imbalance between R1 and R2. Such shifting 171 tends to draw Ve1 and Ve2 upwards during the first pulse phase 30*a*, and downwards during the second pulse phase 30*b* as shown in waveform 182*b*.

In waveform 182*b*, it is assumed that the currents from the DAC circuitry are balanced, with the PDACs and NDAC providing currents of the same magnitude. Icm is therefore zero, which doesn't charge capacitor Cc 152/38. Nonetheless, referencing Ve1 and Ve2 to Vcm may cause the compliance voltage to be too low given the shifting 171, and in waveform 182*b* the compliance voltage has been raised (51, 49) so that Ve1 and Ve2 are still bounded between VH-Vp(min) and Vn(min) to prevent the resulting pulses from becoming loaded.

A comparison of waveforms 182*b* (FIG. 9B) and 180*b* (FIG. 9A) shows that use of the tissue biasing circuitry 150 may warrant increasing the value of the compliance voltage, VH if the resistances between the active electrodes and the case electrode are not balanced. As explained in the '202 patent, VH might need to be increased even further if the currents are imbalanced in addition to the resistance imbalance, although this isn't shown in FIG. 9B.

The foregoing figures illustrate that several different factors can implicate how the compliance voltage VH should be set or adjusted. As shown, use of tissue biasing circuitry 150 to set common mode voltage Vcm in the tissue—as is preferred when sensing neural responses—can require increasing VH. This is particularly true when current or resistance (e.g., impedance) imbalances are present. Further, the presence of a current Icm will cause Vcm to change over time from its nominal value of VH/2 as the common mode capacitor Cc 152/38 charges or discharges. Changing Vcm may require changing VH to prevent loading of the current pulses.

The manner in which Vcm is driven—as programmed by control signals W setting +/−|Iout|—can ultimately affect the compliance voltage VH as well. Setting +/−|Iout| to a large value will tend to keep Vvref=Vref=VH/2. This keeps Vcm more stable, and therefore lessens the need to adjust the VH, but also can increase unwanted stimulation in the tissue in the form of larger currents Icm. Setting+/−|Iout| to a smaller value limits Icm to a lower value, but may cause Vvref to more easily deviate from Vref, which disrupts Vcm, and therefore VH. In other words, VH may require more frequent adjustment when Vvref deviates from Vref.

Ideally, VH is set to a lowest voltage that is sufficient to form the current pulses without loading, so that these pulses are formed at their programmed currents. Also, if tissue biasing circuitry 150 is used to set Vcm in the tissue, it is preferred that Icm be limited to a lowest value +/−|Iout| to minimize unwanted currents in the tissue.

Figure 10:
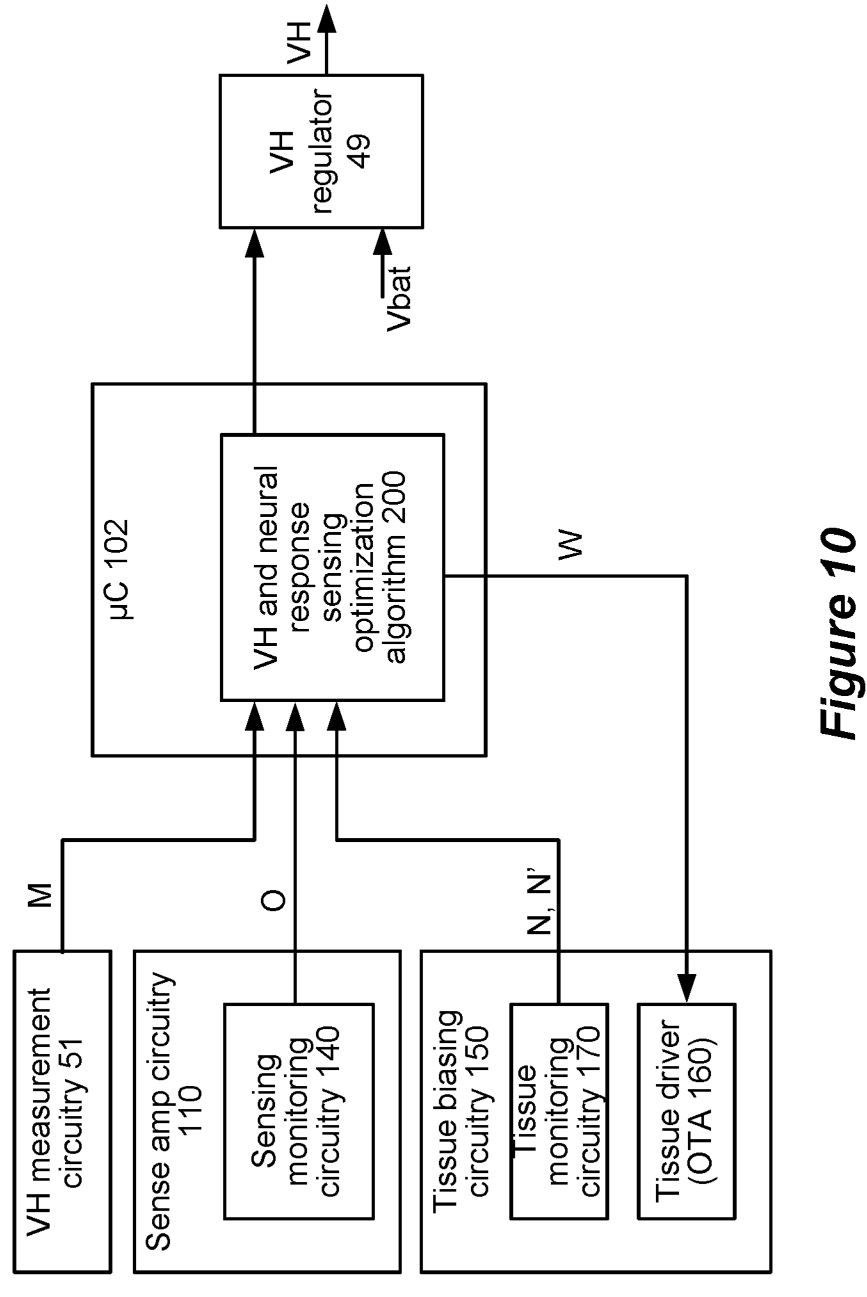
FIG. 10 shows implementation of an optimization algorithm in the control circuitry of the IPG, which is capable of optimizing the stimulation, the sensing electrodes, the compliance voltage, and the strength of tissue drive, when a common mode voltage is provides to the tissue.

The Applicant discloses an optimization algorithm 200 to achieve these goals. As shown in FIG. 10, the algorithm 200 can be programmed as firmware within the IPG's control circuitry 102. The algorithm 200 receives as inputs various control signals output from various measurements circuitry in the IPG explained above. In particular, the algorithm 200 receives control signal M from the VH measurement circuitry 51 (FIG. 3). As described earlier, this control signal can indicate whether the stimulation current is provided by the stimulation circuitry at the prescribed amplitude without loading, and hence whether any of the voltage drops across the active P/NDACs are too low. As noted earlier, if any of the voltage drops are too low, the DACs may not accurately output the programmed current, resulting in loaded current pulses (105, FIG. 9A). In this circumstance, an increase in VH is warranted and would be affected by the VH regulator 49.

The algorithm 200 also receives control signal O issued from the sensing monitoring circuitry 140, which was illustrated in conjunction with the sense amp circuitry 110 (FIG. 8A). As explained above, control signal O informs about the magnitude of the signals at the inputs of the sense amp circuitry, and in particular whether these inputs signals are at proper magnitudes for diff amp operation 130 and hence appropriate for sensing the signals from the patient's tissue. This information is relevant to adjusting HV as well: the inputs to the diff amp 130 are referenced to Vcm in the tissue, which in turn is produced as a function of VH. Adjusting VH will affect the magnitude of these signals, and therefore adjusting VH may bring them to magnitudes appropriate for the diff amp 130.

The algorithm 200 also receives control signals N and N' from the tissue monitoring circuitry, which was illustrated in conjunction with the tissue biasing circuitry 150 (FIGS. 7A & 7B). These control signals N and N' as summarized earlier inform whether Vvref is too high or too low relative to Vref, and hence whether tissue current Icm has been limited to (i.e., reached)+/−|Iout| as programmed. As discussed above, such deviation may suggest that it is reasonable to adjust (increase VH). Additionally, it may be warranted to adjust the tissue drive strength (e.g., to increase +/−|Iout| per control signals W) to allow Vvref to keep parity with Vref, which eases compliance voltage VH regulation.

Note that control signal M, N,N' and O can each comprise one or more control signals, depending on the implantation and the specific circuitry used to generate them.

Figure 11A:
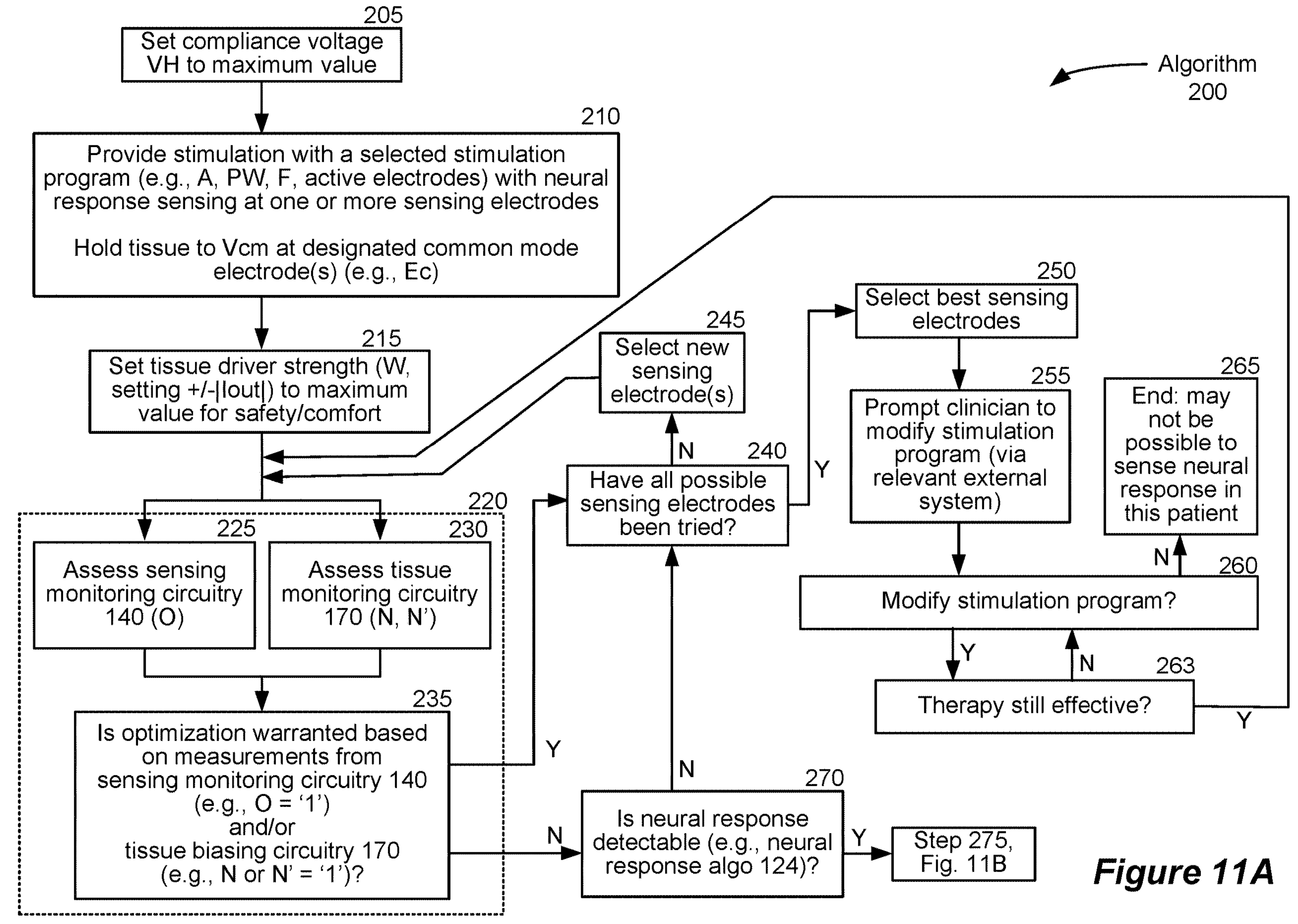
FIGS. 11A and 11B show a flow chart of the optimization algorithm of FIG. 10.
Figure 11B:
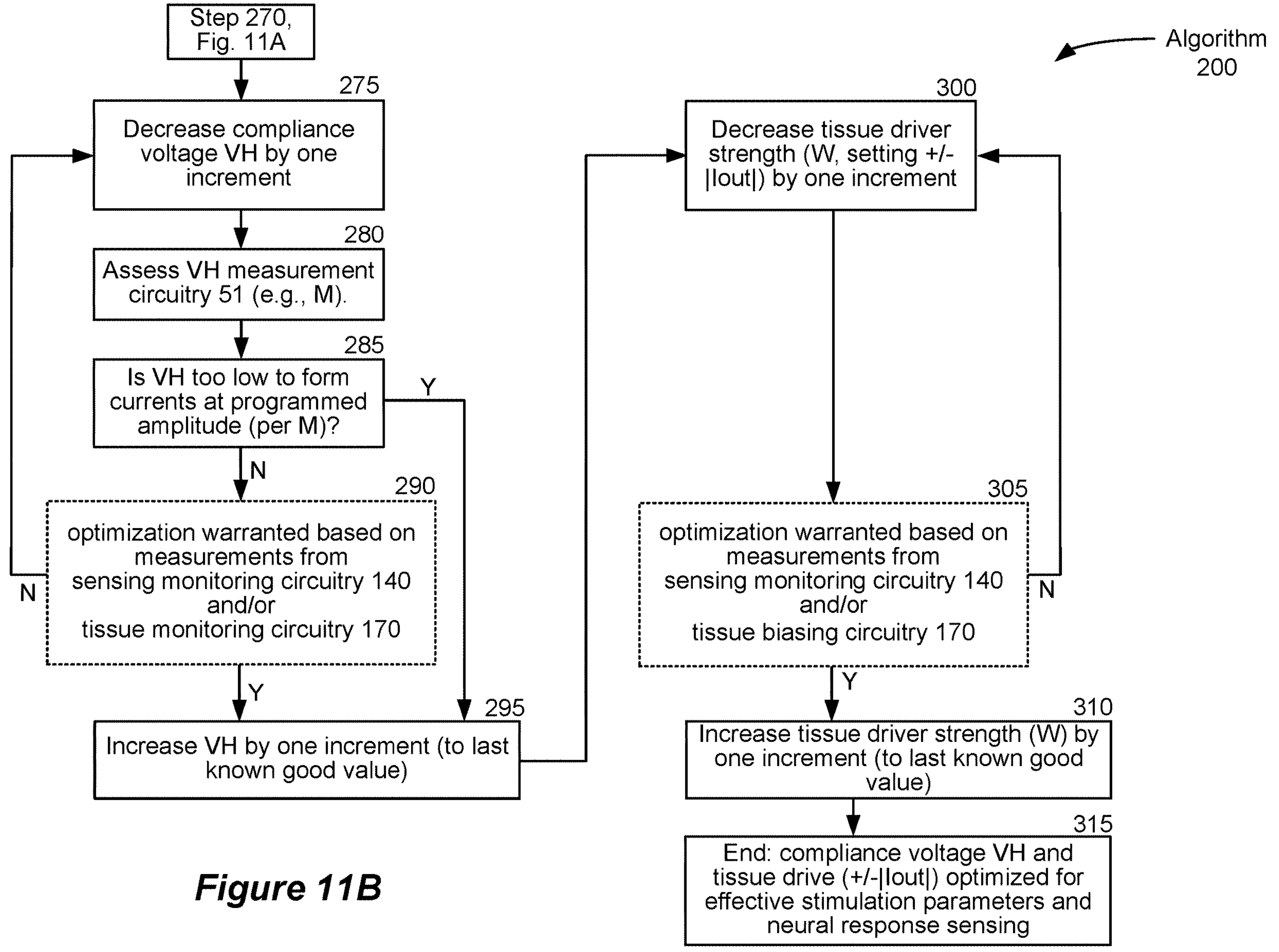

From these control signals, the algorithm 200 can both adjust VH (i.e., by controlling the VH regulator 49), and adjust the tissue drive strength +/−|Iout| provided by the OTA 160 via adjusting control signals W. The details of algorithm 200 are shown in FIGS. 11A and 11B, which set forth a number of steps. In an actual implementation, not all of these steps are strictly necessary, and additional steps not shown could be included. Further, the order of the steps as set forth in algorithm 200 could be varied as well.

While the optimization algorithm 200 is shown as implemented in IPG's control circuitry 102, the algorithm 200 may also involve an external system (FIG. 4) in communication with the IPG, such as a clinician's programmer 70. For example, optimization algorithm 200 can be initiated by a clinician attempting to optimize IPG operation for a patient, using the external system's GUI 99 for example, although this detail isn't shown. The optimization algorithm 200 may also comprise instructions on a non-transitory computer readable media, such as solid-state, magnetic, or optical disk or memory. In this regard, the optimization algorithm 200 may exist on any of the systems used with the IPG, as described earlier in FIG. 4.

In a first step (205), the algorithm 200 programs the VH regulator 49 to produce a maximum value for the compliance voltage, VH. A "maximum" value for VH can comprise a highest VH the IPG is capable of producing (e.g., 15V), or may comprise a sufficiently high value to clearly provide currents without loading as prescribed in the patient's stimulation (discussed next with respect to step 210). As will be explained later, this maximum compliance voltage is preferably decreased to an energy efficient values as the algorithm 200 iterates.

At step 210, the stimulation program for the patient is applied. It is assumed that the stimulation parameters for the stimulation program (e.g., A, PW, F, the selected stimulation electrodes) have been pre-determined and are suitable for addressing the patient's symptoms (e.g., pain) and have been transmitted to the IPG by an external system. It is further assumed at step 210 that neural response sensing (i.e., at sense amp circuitry 110) will accompany the stimulation. As noted earlier, sensing neural responses can be desired for a number of reasons, including possibly controlling or adjusting the stimulation program. At step 210, one or more initial sensing electrodes (e.g., S+, S−) may have been selected, and may be pre-determined as working reasonably well with the stimulation program in question. That being said, the algorithm 200 may further adjust the stimulation electrodes, as discussed further below. Because neural sensing will be used, one or more of the electrodes is also designated to provide a common mode voltage Vcm to the tissue (using tissue biasing circuitry 150). As discussed above, providing a steady common mode voltage Vcm to the tissue can assist with sensing neural response.

At step 215, the tissue driver (e.g., OTA 160) is programmed (by control signals W) to provide a particular tissue drive strength (i.e., to set the magnitude of +/−|Iout| output by the OTA). Preferably, this drive strength is programmed to a maximum value, which at least initially in the algorithm permits a maximum unprescribed current |Icm| to flow in the tissue. A "maximum" value for +/−|Iout| comprise a highest magnitude the IPG (i.e., the OTA 160) is capable of producing, or may otherwise comprise a sufficiently high value that is comfortable or safe for the patient. Testing may be performed at this step to set +/−|Iout| (per W) at a highest value the patient can tolerate. As will be explained later, this maximum tissue drive strength is preferably decreased as the algorithm 200 iterates.

Step 220 is shown having different substeps, but in sum generally assesses whether one or more of the measurement sub-systems indicates that optimization might be warranted. Specifically, sensing monitoring circuitry 140 can be assessed in step 225, and its control signal O assessed to see whether the inputs X+ and X− to the sense amp circuitry are at a improper level for neural response sensing (O='1'). Similarly, tissue monitoring circuitry 170 can be assessed in step 230, and its control signals N,N' are assessed to see whether Vvref has significantly deviated from Vref (N,N'='1'). It certain instances, it may only be necessary to perform only one of step 225 or 230, or both of these steps can be performed.

Regardless, in step 235, the algorithm determines whether optimization might be warranted, and if so the algorithm proceeds to step 240. In this step, the algorithm 200 inquires whether there may be other sensing electrodes to select, and if so, may select such new sensing electrodes at step 245. Steps 240 and 245 recognize that if conditions are not optimized for sensing (step 220), a solution may be to adjust the sensing electrodes initially chosen. Different sensing electrodes would receive different signals with different magnitudes, and might be more appropriate for sensing given the stimulation in question (step 210). The selection of new sensing electrodes at step 245 may be automated by the algorithm 200, or can occur with clinician assistance. In this regard, algorithm 200 may communicate with an external system (e.g., clinician programmer 70) to prompt the clinician to consider (e.g., at GUI 99) selecting new sensing electrodes. If new sensing electrodes are selected in step 245, the algorithm 200 can again assess whether optimization is warranted in light of the measurements made in step 220, which may result in selecting new sensing electrodes again at step 245.

If at step 240 all possible sensing electrodes have been tried, providing neural sensing for the patient in question may be difficult to achieve, in particular because the compliance voltage VH and tissue drive +/−|Iout| have been maximized (steps 205, 215) and may not be able to be further increased. This may warrant changing the stimulation program for the patient, if possible. First, the algorithm 200 can select best of the sensing electrodes in step 250, based on the measurements taken while different sensing electrodes were tried earlier (steps 240, 245), which may be logged in the control circuitry 102. For example, the algorithm 200 may select sensing electrodes used when the various control signals O, N and N' were unsuitable ('1') for the shortest length of time.

At step 255, the algorithm 220 may communicate with the external system to prompt the clinician (GUI 99) to consider modifying the patient's stimulation program at step 260. This may be reasonable even though the patient's stimulation program is already suitable to treat the patient. Small changes to the stimulation program may be possible that would ease VH generation and sensing in the IPG, while still not significantly affecting the patient's therapy. For example, if high amplitude (A) pulses are used, perhaps this amplitude can be reduced to reduce the need for a high compliance voltage VH. Such an adjustment can be accompanied by other adjustments, such as by increasing the pulse width (PW), or increasing the frequency (F), to offset the loss of stimulation energy caused by the reduction in amplitude. Additionally, the high amplitude current may be reduced by sharing this current at least in part with another (neighboring) stimulation electrodes, thus reducing the amplitude at any given electrode. At step 260, the algorithm 200 may also automatically modify the situation program in these or other ways.

If in step 260 the clinician modifies the stimulation program (or the algorithm 200 does so automatically), step 263 inquires whether this modified program is still effective for the patient. Therapeutic effectiveness may be gauged in consultation with the patient, and/or via receipt of other measurements, as understood by those skilled in the art. If the therapy is not therapeutically effective, it may be modified again (step 260). Ultimately, if the stimulation program cannot be suitably modified, or if the clinician doesn't wish to modify the stimulation program, it may not be possible to provide neural sensing in conjunction with the patient's stimulation program (step 265). In this circumstance, the algorithm 200 may disable the IPG's sense amp circuitry 110 and the tissue biasing circuitry 150.

If the stimulation program as modified provides effective therapy for the patient (step 263), the algorithm 200 can return to step 220 (and its substeps) to assess whether further optimization is warranted based on the reported control signals discussed above. If not, a neural response should be detectable, and this can be verified at step 270. This can involve for example providing digitized neural responses to the neural response algorithm 124 (FIG. 5) to see if relevant features can be successfully extracted from the neural response. If not, the sensing electrodes and/or the stimulation program may again be adjusted (steps 240, 245, etc.).

If a neural response is successfully detected at step 270, the algorithm 200 can proceed to optimize the compliance voltage VH and the tissue drive strength +/−|Iout|, as shown in FIG. 11B. Up to this point, these parameters were maximized (steps 205, 215), which eases providing stimulation and sensing. However, having VH higher than necessary for the stimulation program wastes power in the IPG. And having the tissue drive higher than necessary for proper sensing runs the risk of unwanted currents through the tissue (Icm). Next steps are therefore designed to decrease these parameters while still providing suitable stimulation and sensing performance.

At step 275, the compliance voltage VH is decreased to a lower value by having the algorithm 200 control the VH regulator 49 (FIG. 3) accordingly. Preferably, this involve decreasing VH by a minimum increment.

Decreasing VH runs the risk that the stimulation may not be provided at programmed levels (i.e., the pulses may become loaded), and so in step 280 the VH measurement circuitry 51 is assessed (control signal M), and a determination is made whether any of the voltage drops across the active P/NDAC are too low in step 285. If so, the algorithm 200 in step 295 increases VH by one increment, or to a last known good value where the pulses were not loaded. If VH is not too low at step 285, the algorithm 200 assesses at step 290 whether optimization is warranted by assessing either or both of the sensing monitoring circuitry 140 (control signal O) or the tissue monitoring circuitry (control signals N and N'). This can be the same analysis that was made earlier in step 220 (FIG. 11A). If optimization is warranted at step 290, this suggests that decreasing VH earlier (step 275) has negatively impacting sensing and/or Vcm generation in the tissue, and so VH is again adjusted upwards in step 295.

If optimization does not appear warranted at step 290, the compliance voltage can be decreased further at step 275, and with steps 280-290 repeated. As VH is decreased, VH will eventually either become too low to properly form the stimulation without loading (step 285), or too low for proper sensing and/or Vcm generation in the tissue. Upon the first of these occurrences, the algorithm at step 295 will increase VH (again by an increment or to a last known good value). Once the algorithm has reached this point, the compliance voltage VH is optimized. It is as low as possible, which saves power in the IPG. It's also high enough that the current pulses are formed within loading, and without affecting neural response sensing or tissue voltage (Vcm) generation.

At this point, the algorithm 200 can move to steps designed to adjust the tissue drive strength +/−|Iout| if desired, although these steps could also be omitted. Preferably, this drive is no stronger than necessary, which minimizes the magnitude of inadvertent, non-therapeutic currents in the tissue (Icm). At step 300, the strength of the tissue driver (e.g., OTA 160) is decreased (per control signals W), preferably by one increment. At step 305, the algorithm 200 assesses whether optimization is warranted by assessing either or both of the sensing monitoring circuitry 140 (control signal O) or the tissue monitoring circuitry (control signals N and N'), which again can be similar to what occurred in step 220 (FIG. 11A). If optimization is not warranted, because neural response sensing and tissue biasing are within limits per control signals O, N and N', the strength of the tissue driver can again be decreased at step 300, and step 305 repeated.

Eventually, as the tissue drive strength +/−|Iout| is decreased, it will eventually begin to affect either or both of neural response sensing or tissue biasing. As discussed earlier, decreasing +/−|Iout| limits Icm in the tissue, which could eventually cause Icm to reach +/−|Iout| and Vvref to deviate from Vref. This can affect Vcm, and ultimately VH. This will eventually require optimization at step 305 based upon the measurements reported by the sensing monitoring circuitry 140 (e.g., O='1') and/or the tissue monitoring circuitry 170 (N or N'='1'), and so at step 310 the tissue drive strength can be increased (W) by an increment or to the last known good value.

At this point (step 315), optimization is complete for the patient. Suitable sensing electrodes have been chosen, and possibly adjusted if necessary, and the stimulation program has also possibly been modified to allowing tissue voltage biasing (Vcm) and neural response sensing to occur. Further, the compliance voltage VH and the tissue drive strength (+/−|Iout|) used to produce Vcm have been optimized to the lowest levels possible for the stimulation program in question.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for operating a stimulator device having a plurality of electrodes comprising at least one sensing electrode, at least two stimulation electrodes, and at least one common mode electrode, the method comprising:

receiving signals from a patient's tissue at the at least one sensing electrode, and providing the received signal to at least one input of a sense amp circuit;

providing a common mode voltage to the tissue at the at least one common mode electrode, wherein a tissue current at the common mode electrode is limited to a programmable first magnitude;

executing a stimulation program to provide a stimulation current of a prescribed amplitude between the at least two stimulation electrodes and through the patient's tissue using stimulation circuitry powered by a compliance voltage;

generating at least one first control signal indicating whether the tissue current has reached the first magnitude;

generating at least one second control signal indicating whether a second magnitude at the at least one input is appropriate for sensing the signals from the patient's tissue;

generating at least one third control signal indicating whether the stimulation current is provided by the stimulation circuitry at the prescribed amplitude without loading; and executing an algorithm in the stimulator device, wherein the algorithm is configured to use the at least one first control signal, the at least one second control signal, and the at least one third control signal to adjust the compliance voltage.

2. The method of claim 1, wherein the algorithm is configured to adjust the compliance voltage to a lowest value at which the stimulation current is provided by the stimulation circuitry at the prescribed amplitude without loading; and either or both of the following occurs:

the tissue current has not reached the first magnitude, or the second magnitude at the at least one input is appropriate for sensing the signals from the patient's tissue.

3. The method of claim 2, wherein the algorithm is configured to initially set the compliance voltage to a maximum voltage.

4. The method of claim 1, wherein the algorithm is further configured to use either or both of the at least one first control signal and the at least one second control signal to adjust the first magnitude.

5. The method of claim 4, wherein the algorithm is configured to adjust the first magnitude to a lowest value at which either or both of the following occurs:

the tissue current has not reached the first magnitude, or the second magnitude at the at least one input is appropriate for sensing the signals from the patient's tissue.

6. The method of claim 4, wherein the algorithm is configured to adjust the compliance voltage before adjusting the first magnitude.

7. The method of claim 4, wherein the algorithm is configured to adjust the first magnitude using the at least one first control signal.

8. The method of claim 4, wherein the algorithm is configured to adjust the first magnitude using the at least one second control signal.

9. The method of claim 4, wherein the algorithm is configured to adjust the first magnitude using the at least one first control signal and the at least one second control signal.

10. The method of claim 4, wherein the algorithm is configured to initially set the first magnitude to a maximum value.

11. The method of claim 10, wherein the algorithm is configured to use either or both of the at least one first control signal and the at least one second control signal to reduce the first magnitude to a lowest value.

12. The method of claim 1, wherein the algorithm is further configured to select at least one of the electrodes as the at least one sensing electrode.

13. The method of claim 12, wherein the algorithm is further configured to select at least one of the electrodes as the at least one sensing electrode prior to adjusting the compliance voltage.

14. The method of claim 13, wherein the algorithm selects the at least one sensing electrode upon determining that either or both of the following occurs:

the tissue current has not reached the first magnitude, or the second magnitude at the at least one input is appropriate for sensing the signals from the patient's tissue.

15. The method of claim 1, wherein the algorithm is further configured to modify or suggest a modification to the stimulation program.

16. The method of claim 15, wherein the algorithm is configured to continue modifying or suggesting the modification to the stimulation program until determining that either or both of the following occurs:

the tissue current has not reached the first magnitude, or the second magnitude at the at least one input is appropriate for sensing the signals from the patient's tissue.

17. A stimulator device having a plurality of electrodes comprising at least one sensing electrode, at least two stimulation electrodes, and at least one common mode electrode, the device comprising:

a sense amp circuit configured to receive at at least one input signals from a patient's tissue at the at least one sensing electrode;

tissue driver circuitry configured to provide a common mode voltage to the tissue at the at least one common mode electrode, wherein a tissue current at the common mode electrode is limited to a programmable first magnitude;

stimulation circuitry configured to execute a stimulation program to provide a stimulation current of a prescribed amplitude between the at least two stimulation electrodes and through the patient's tissue, wherein the stimulation circuitry is powered by a compliance voltage;

first measurement circuitry configured to generate at least one first control signal indicating whether the tissue current has reached the first magnitude;

second measurement circuitry configured to generate at least one second control signal indicating whether a second magnitude at the at least one input is appropriate for sensing the signals from the patient's tissue;

third measurement circuitry configured to generate at least one third control signal indicating whether the stimulation current is provided by the stimulation circuitry at the prescribed amplitude without loading; and control circuitry programmed with an algorithm, wherein the algorithm is configured to use the at least one first control signal, the at least one second control signal, and the at least one third control signal to adjust the compliance voltage.

* * * * *